(12) United States Patent
Wang et al.

(10) Patent No.: US 11,219,397 B2
(45) Date of Patent: Jan. 11, 2022

(54) SENSOR MODULE FOR VITAL SIGN MONITORING DEVICE

(71) Applicant: ANALOG DEVICES, INC., Norwood, MA (US)

(72) Inventors: Weidong Wang, Westford, MA (US); David Frank Bolognia, Charlestown, MA (US); Michelle A. Farrington, Arlington, MA (US); Roberto Munoz, Alboraya (ES); Michael Alan Falter, Windham, NH (US); Patrick Riehl, Lynnfield, MA (US)

(73) Assignee: Analog Devices, Inc., Norwood, MA (US)

( * ) Notice: Subject to any disclaimer, the term of this patent is extended or adjusted under 35 U.S.C. 154(b) by 223 days.

(21) Appl. No.: 16/008,930

(22) Filed: Jun. 14, 2018

(65) Prior Publication Data

US 2018/0360341 A1   Dec. 20, 2018

Related U.S. Application Data

(60) Provisional application No. 62/520,437, filed on Jun. 15, 2017.

(51) Int. Cl.
*A61B 5/259*   (2021.01)
*A61B 5/00*    (2006.01)
(Continued)

(52) U.S. Cl.
CPC ............ *A61B 5/259* (2021.01); *A61B 5/0006* (2013.01); *A61B 5/0008* (2013.01);
(Continued)

(58) Field of Classification Search
None
See application file for complete search history.

(56) References Cited

U.S. PATENT DOCUMENTS

2004/0215098 A1 * 10/2004 Barton ................ A61B 5/0008
                                                      600/549
2007/0123756 A1   5/2007 Katajima et al.
(Continued)

FOREIGN PATENT DOCUMENTS

CN     206007221 U    3/2017
EP       2783725 A   10/2014
(Continued)

OTHER PUBLICATIONS

Office Action issue in Japanese application No. 2018-114425 dated Dec. 9, 2019.
(Continued)

*Primary Examiner* — Jonathan T Kuo
(74) *Attorney, Agent, or Firm* — Knobbe, Martens, Olson & Bear LLP

(57) ABSTRACT

A sensor module for a wearable vital sign monitoring device is disclosed. The sensor module includes a substrate having a first side and a second side opposite the first side. The sensor module also includes a sensor die mounted to the first side of the substrate. The sensor die is configured to monitor a vital sign of a user. The sensor module further includes a waterproof coating that conformally covers the sensor die, at least a portion of the first side of the substrate, and at least a portion of the second side of the substrate.

20 Claims, 21 Drawing Sheets

(51) Int. Cl.
*A61B 5/145* (2006.01)
*A61B 5/1455* (2006.01)
*A61B 5/0205* (2006.01)
*A61B 5/287* (2021.01)
*A61B 5/11* (2006.01)
*A61B 5/024* (2006.01)
*A61B 5/01* (2006.01)

(52) U.S. Cl.
CPC .......... *A61B 5/0205* (2013.01); *A61B 5/1455* (2013.01); *A61B 5/14532* (2013.01); *A61B 5/287* (2021.01); *A61B 5/681* (2013.01); *A61B 5/6804* (2013.01); *A61B 5/6833* (2013.01); *A61B 5/0002* (2013.01); *A61B 5/01* (2013.01); *A61B 5/024* (2013.01); *A61B 5/11* (2013.01); *A61B 2560/0214* (2013.01); *A61B 2562/18* (2013.01)

(56) References Cited

U.S. PATENT DOCUMENTS

| | | | | |
|---|---|---|---|---|
| 2010/0217158 | A1* | 8/2010 | Wolfe | A61B 5/113 600/595 |
| 2013/0041235 | A1* | 2/2013 | Rogers | A61B 5/1107 600/306 |
| 2013/0317333 | A1 | 11/2013 | Yang et al. | |
| 2014/0121473 | A1* | 5/2014 | Banet | A61B 5/6808 600/301 |
| 2014/0276167 | A1 | 9/2014 | Dasgupta et al. | |
| 2016/0174840 | A1 | 6/2016 | Udoh et al. | |
| 2016/0242654 | A1* | 8/2016 | Quinlan | A61B 5/04087 |
| 2017/0202459 | A1* | 7/2017 | Cao | A61B 5/0006 |
| 2018/0360352 | A1 | 12/2018 | Ohno | |

FOREIGN PATENT DOCUMENTS

| | | |
|---|---|---|
| JP | H04-215739 | 8/1992 |
| JP | 2007-105316 A | 4/2007 |
| JP | 2007-209374 A | 8/2007 |
| JP | 2015-504338 A | 2/2015 |
| JP | 2017-500076 A | 1/2017 |
| WO | WO 2013/177323 A1 | 11/2013 |
| WO | WO 2015/066430 A1 | 5/2015 |
| WO | WO 2017/094089 A1 | 6/2017 |

OTHER PUBLICATIONS

Office Action issued in Japanese application No. 2018-114425 dated Jun. 10, 2019.
Office Action issue in European application No. 18177464.7 dated Jan. 10, 2020.
Partial European Search Report dated Sep. 26, 2018, issued for European Patent Application No. 18177464.7, 13 pages.

* cited by examiner

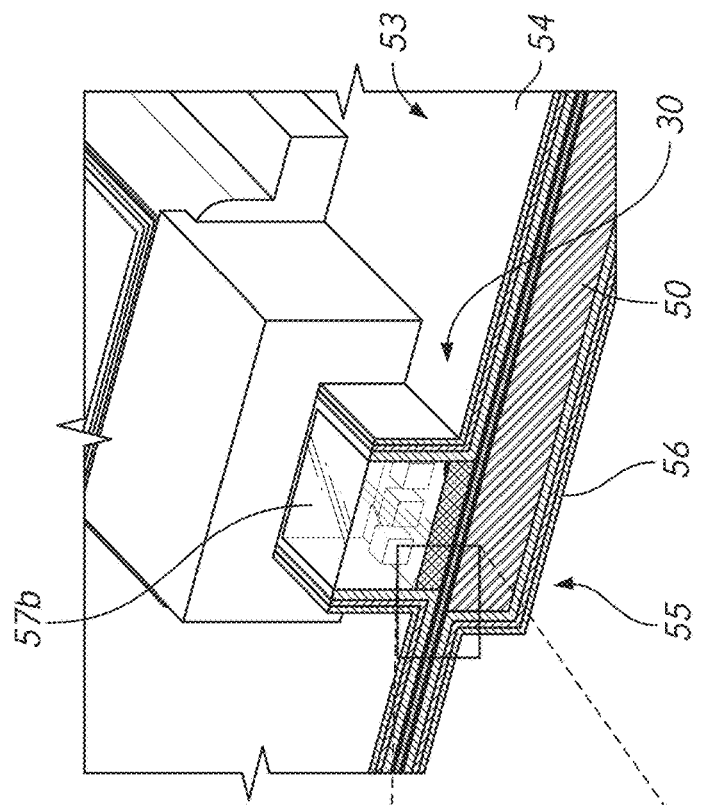
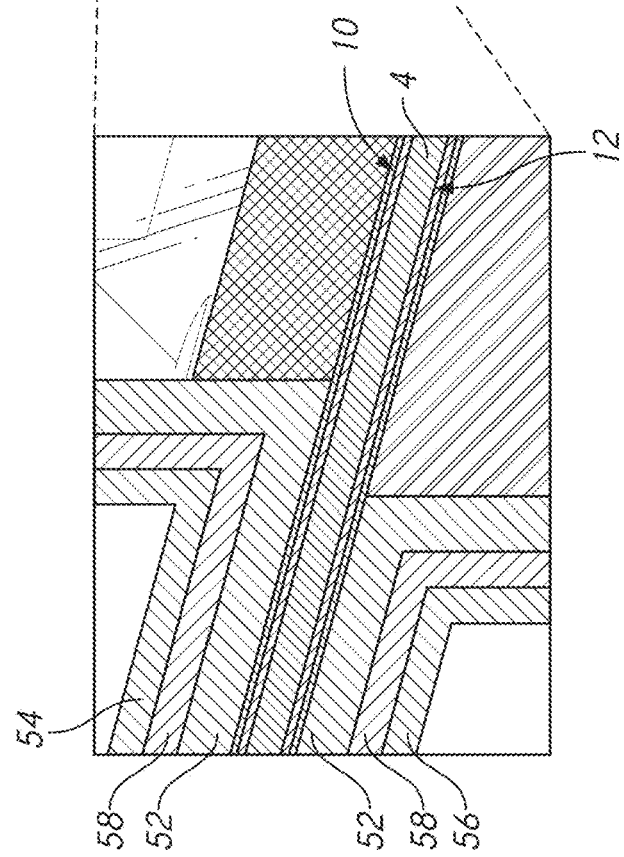
FIG. 6A
FIG. 6B

| Layer | Thickness (um) | Ranges |
|---|---|---|
| Top release liner | 50 | +/-5um |
| Adhesive | 50 | +/-5um |
| Top cloth | 50 | +/-5um |
| Adhesive | 50 | +/-5um |
| Conformal coating | 75 | +/-7.5um |
| Top SR (e.g., solder mask) | 10 | +/-1um |
| Top Cu | 12 | +/-1um |
| Flex core PI | 50 | +/-5um |
| Bottom Cu | 12 | +/-1um |
| Bottom SR (e.g., solder mask) | 10 | +/-1um |
| Conformal coating | 75 | +/-7.5um |
| Conductive adhesive | 51 | +/-5um |
| Conductive cloth | 76 | +/-7.5um |
| Adhesive | 50 | +/-5um |
| Bottom cloth | 50 | +/-5um |
| Total | 671 | +/-70um |

FIG. 14

SENSOR MODULE FOR VITAL SIGN MONITORING DEVICE

CROSS-REFERENCE TO RELATED APPLICATIONS

This application claims priority to U.S. Provisional Patent Application No. 62/520,437, filed Jun. 15, 2017, the entire contents of which are hereby incorporated by reference herein in their entirety and for all purposes.

BACKGROUND

Field

The field relates to a sensor module for a wearable vital sign monitoring device.

Description of the Related Art

Systems and devices for monitoring vital signs can track a user's heart rate, cardiac electric activity, user movements, and other biological signals representative of a state of the user's anatomy. Some vital sign monitoring (VSM) devices can be worn or carried by the user, such that the user may expose the VSM device to various environments. The VSM device can include various sensing and/or processing electronics which may be sensitive to such environments. Accordingly, there remains a continuing need for improved protection of VSM devices from the environments into which they are introduced.

SUMMARY

In one aspect, a sensor module for a wearable vital sign monitoring device is disclosed. The sensor module includes a substrate that has a first side and a second side opposite the first side. The module also includes a sensor die mounted to the first side of the substrate. The sensor die configured to monitor a vital sign of a user. The module further includes a waterproof coating conformally covering the sensor die, at least a portion of the first side of the substrate, and at least a portion of the second side of the substrate.

In one embodiment, the sensor module further includes an electrode disposed on the second side of the substrate. The electrode can be positioned within an opening in the waterproof coating. The sensor die can be configured to process signals transduced by the electrode.

In one embodiment, the sensor die comprises an optical sensor. The waterproof coating can include a window over a portion of the optical sensor.

In one embodiment, the sensor module further includes a battery mounted to the first side of the substrate. The first waterproof coating can conformally cover the battery. The sensor module can also include a battery charging coil that is electrically connected to the battery.

In one embodiment, the sensor module further includes a first cover over the first waterproof coating and a second cover over the second waterproof coating. The first and second covers can be joined about a periphery of the substrate such that the substrate is embedded between the first and second covers. The second cover can comprise a conductive cloth. The sensor module can further include an electrode. The electrode can be disposed between the conductive cloth and the substrate. The substrate comprises traces that electrically connect the electrode and the sensor die.

In one embodiment, the substrate and the waterproof coating are flexible. The substrate has a flexible radius of about 5 cm (e.g., 3 cm to 7 cm).

In one aspect, a sensor module for a wearable vital sign monitoring device is disclosed. The sensor module includes a substrate that has a first side and a second side opposite the first side. The sensor module also includes a plurality of electronic components that are mounted to the first side of the substrate. The sensor module further includes a contact on the second side of the substrate. The contact is configured to electrically connect to an electrode pad or a temperature sensor pad. The sensor module includes a waterproof coating that comprises a conformal coating. The waterproof coating covers at least a portion of the first side of the substrate, and at least a portion of the second side of the substrate.

In one embodiment, the plurality of electronic components comprise a sensor die that is configured to process signals transduced by the electrode pad or the temperature sensor.

In one embodiment, the plurality of electronic components comprises a photodetector and a light emitting diode (LED). The waterproof coating can include a window over a portion of the photodetector.

In one aspect, a waterproof sensor module is disclosed. The sensor module includes a substrate that has a first side and a second side opposite the first side. The sensor module also includes a sensor assembly integrated with the substrate. The sensor module further includes a conformal coating that conformally covers at least a portion of the first side of the substrate, and at least a portion of the second side of the substrate.

In one embodiment, the sensor assembly comprises a processor die and an electrode. The processor die can be configured to process signals transduced by the electrode.

In one embodiment, the sensor assembly comprises a photodetector and a light emitting diode (LED).

In one embodiment, the waterproof sensor module further includes a cover attached to at least a portion of the conformal coating.

BRIEF DESCRIPTION OF THE DRAWINGS

These aspects and others will be apparent from the following description of preferred embodiments and the accompanying drawings, which are meant to illustrate and not to limit the invention, wherein:

FIG. 6A is a cross sectional view of a light emitting diode (LED) of the photometric island of the module.

FIG. 6B is a magnified view of the cross section of FIG. 5A showing layers formed thereof.

FIG. 14 is a list of example thickness values for various layers of the sensor module.

DETAILED DESCRIPTION

Figure 1:
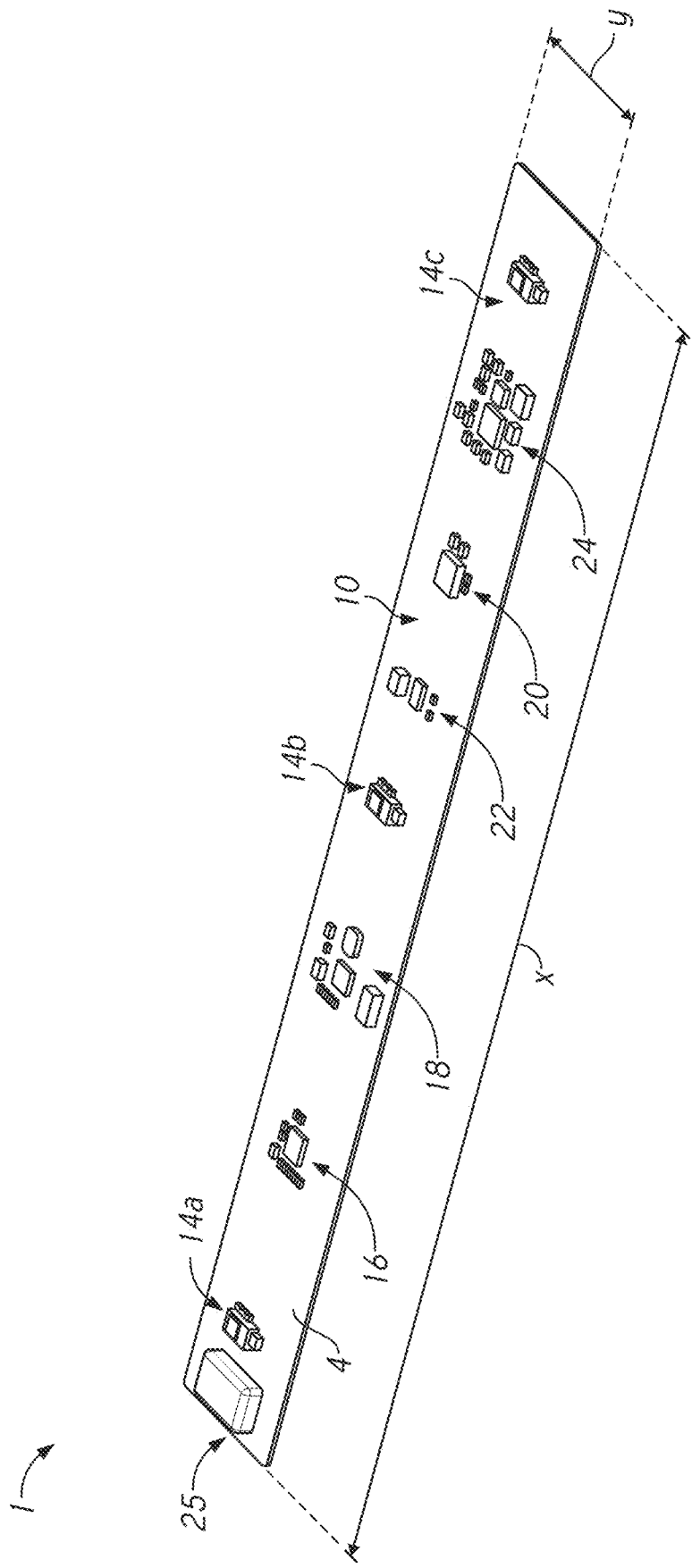
FIG. 1 is a schematic perspective view of a first side of a sensor module according to one embodiment.

Various embodiments disclosed herein relate to a sensor module for a vital sign monitoring (VSM) device. The VSM devices can be worn or carried by a human user and can monitor various types of biological signals representative of the user's anatomy. For example, the VSM devices disclosed herein can monitor one or more of body temperature, heart rate, cardiac electrical activity (e.g., electrocardiogram or ECG), glucose monitoring, heart rate, user motion, etc. The VSM devices can comprise a sensor module with one or more integrated device dies configured to sense and/or process biological signals. The various integrated device dies (e.g., sensor dies, processor dies, etc.), batteries, and other components may be sensitive to moisture or liquids. For example, liquids or moisture may cause circuitry of the devices to short and/or may otherwise damage the components.

In some embodiments, the sensor modules disclosed herein may be integrated into clothing of the user or may be attached directly to the user. In such embodiments, the user may expose the sensor module to wet, moist, or otherwise contaminated environments. Moreover, for embodiments in which the sensor module is integrated into the user's clothing, the user may desire to wash the clothing and the attendant sensor module, e.g., in a washing machine. The use of sensor modules in such wet and/or agitating environments risks the introduction of moisture or liquids into the module, which can damage the electronic components (e.g., device dies, batteries, etc.). Wearable devices are often protected by hermetically sealed housings, but such solutions can limit applications. Accordingly, there remains a continuing need for improved protection of sensor modules for wearable vital sign monitoring devices from environmental contaminants such as water.

In various embodiments, the VSM device can comprise a sensor module comprising one or more integrated device dies mounted to a substrate. For example, the sensor module can comprise a sensor including one or more sensor dies mounted to a first side of the substrate. The sensor die(s) can comprise any suitable sensing die configured to monitor a vital sign of a user. For example, as explained herein and in FIGS. 1-18, the sensor die(s) can comprise optical sensor die(s) (e.g., the photometric islands illustrated in FIGS. 1-2F), a monitoring die for processing electrical signals from electrodes or ECG pads that contact the user's body (e.g., a heart monitor), a motion sensor die (e.g., accelerometer, gyroscope, etc.), and any other types of sensor dies. Moreover, one or more processor dies (e.g., analog-to-digital converter, digital-to-analog converter, general purpose processor and/or Application Specific Integrated Circuit dies) may be mounted to and electrically connected to the substrate. The processor die(s) can be configured to process signals transduced by the sensor die(s). The substrate can comprise any suitable type of substrate, such as a flexible substrate comprising a core, metallic traces on the core, and non-conductive material selectively exposed or provided over the metallic traces. The sensor and/or processor die(s) can be electrically connected to the substrate in any suitable manner, e.g., by way of a flip chip connection, wire bonding, etc. In some embodiments, a battery and other power management devices can be mounted to the first side of the substrate. In some embodiments, antennas (e.g., a chip antenna or a printed antenna formed on the substrate) can be provided on the first side of the substrate. Communications dies can be configured to wirelessly process signals received and/or transmitted by the sensor module. A microcontroller can be provided on the first side to control the operation of the sensor module.

In some embodiments, a second side of the substrate opposite the first side can include other components used in connection with the VSM device. For example, the second side can include a battery or other power management components in some embodiments (see, e.g., FIGS. 4A-4B). In some embodiments, the second side can include interfacing features, such as ECG pads or electrodes configured to transduce or detect electrical signals from a patient's heart. In some embodiments, the first side can be configured to face the user (e.g., the user's skin), and the second side can be configured to face away from the user. For example, in optical sensing embodiments, the first side (to which optical sensing dies may be mounted) of the substrate can be configured to face the user's body so as to transmit and/or receive light from the user's body representative of a biological signal (see FIG. 1). In other embodiments, the second side can be configured to face the user's body and the first side can face away from the user's body. For example, in embodiments that utilize ECG measurements, the ECG pads or electrodes can be disposed on the second side and can be configured to contact the user (e.g., the user's skin). The ECG pads can communicate with the first side by way of metallic traces. Corresponding sensor dies can be configured to process the signals transduced by the ECG pads, and can be disposed on the first side of the substrate facing away from the user (see FIGS. 7-16C).

As explained above, it can be important to waterproof the sensor module so as to withstand wet or moist environments, such as washing machines, swimming pools, showers, bathtubs, etc. In various embodiments, a waterproof coating can conformally cover the sensor die, at least a portion of the first side of the substrate, and at least a portion of the second side of the substrate. The waterproof coating can follow or conform to a surface contour and/or a surface topology of the structures underlying the coating, e.g., the integrated device dies, the substrate, etc. For example, in some embodiments, the coating can conform to upper surfaces of the components, side surfaces of the components, and corner regions. In some embodiments, the waterproof coating may be more flexible than the substrate. In some embodiments, an electrode can be disposed on the second side of the substrate, with the electrode positioned within an opening in the waterproof coating. Beneficially, a battery can be provided in the sensor module such that the sensor module need not connect to a power source by wires. The battery can comprise a rechargeable battery or a non-rechargeable battery in various arrangements. The device can be configured with a battery charge coil (see, e.g., FIG. 12) for wirelessly recharging the battery to obviate access to the battery beneath the waterproof coating. In some embodiments, the battery can be mounted to the first side of the substrate, with the first waterproof coating conformally covering the battery. In some embodiments, a first cover can be disposed over the first waterproof coating and a second cover can be disposed over the second waterproof coating. The first and second covers can be joined about a periphery of the substrate such that the substrate is embedded between the first and second covers. In some embodiments, the second cover can comprise conductive cloth patches over electrodes. In embodiments that utilize ECG measurements, the conductive cloth can provide electrical communication between the ECG pads and the analyte, such as a user's skin.

Turning to FIGS. 1-6B, embodiments of a sensor module 1 comprising optical sensor devices are disclosed. The sensor module 1 of FIGS. 1-6B can optically detect various biological signals representative of, for example, heart rate, blood glucose, etc.

FIG. 1 is a schematic perspective view of the module 1. As shown in FIG. 1, a plurality of integrated device dies can be disposed on a first side 10 of the substrate 4, which can be configured to face the user during operation. Optical sensor devices can be provided on photometric islands 14a, 14b, 14c on the first side 10. A microcontroller 16, an antenna assembly 18, an accelerometer 20, an optical analog front end (AFE) 22, power management devices 24, and a connector 25 can also be provided on the first side 10. Though there are three photometric islands 14a, 14b, 14c, and one AFE 22 are illustrated in FIG. 1, there may be any number of the photometric islands 14a, 14b, 14c and AFE 22 disposed on the substrate 4. For example, in some embodiments, the sensor module 1 can include five photometric islands with two AFEs, three photometric islands with three AFEs, etc. Beneficially, the embodiments disclosed herein can be self-contained to include, e.g., on-board power supply (e.g., battery), power management, sensing, processing, and wireless communications, such that significant processing capabilities can be provide within the module. In some embodiments, the sensor module 1 can be disposed in a cavity to further protect or package the device. For example, the sensor module 1 can be disposed in a flexible housing that defines a cavity into which the sensor module 1 can be inserted.

Figure 2B:
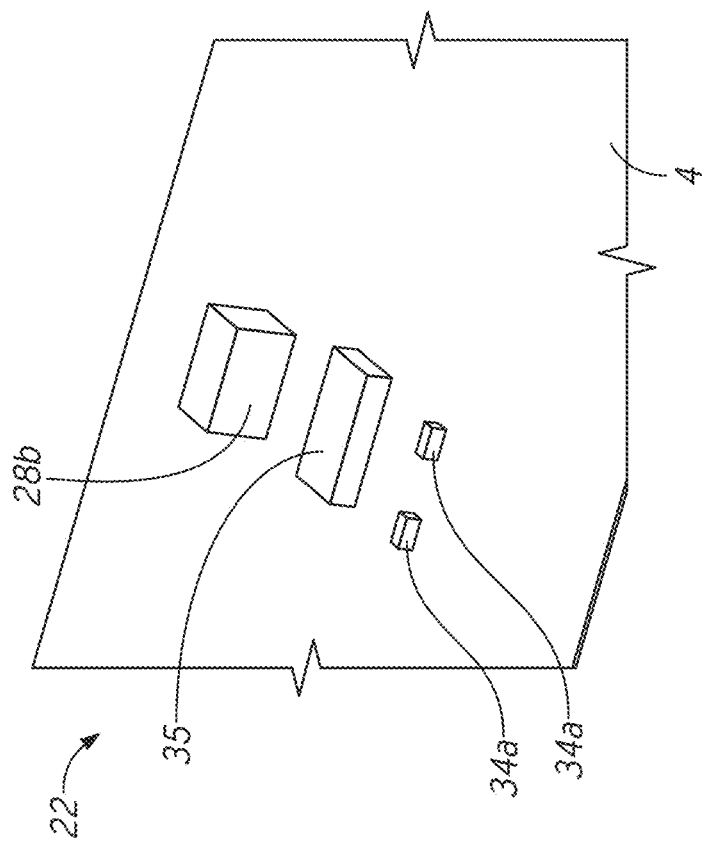
FIG. 2B is a schematic perspective view of an optical analog front end (AFE) mounted to the first side of the substrate of the sensor module of FIG. 1.
Figure 2A:
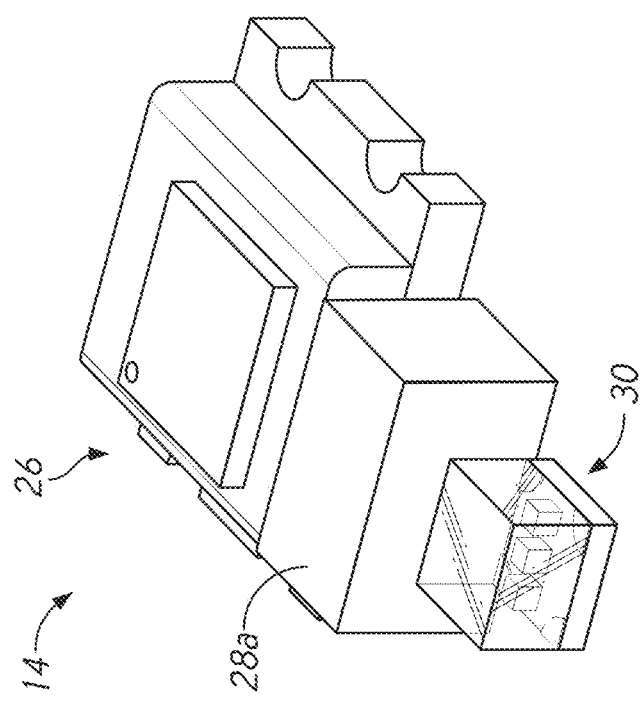
FIG. 2A is a schematic perspective view of a photometric island mounted to a first side of a substrate of the sensor module of FIG. 1.

FIG. 2A shows the photometric island 14a, 14b, 14c that includes a photodetector 26, a capacitor 28, and a light emitting diode (LED) 30 electrically connected to one another. In some embodiments, when the photodetector 26, the capacitor 28, and the LED 30 are mounted on the substrate 4, shown at least in FIG. 1. For example, traces embedded in the substrate may make the electrical connection. In some embodiments, light from the LED 30 (which may comprise an RGB LED) can be emitted towards the user and can be reflected back to the photodetector 26. The detected light can be processed to determine various types of vital signs of the user. In some embodiments, the photodetector 26 and the LED 30 may be packaged together.

FIG. 2B shows the optical AFE 22 disposed on the first side 10 of the substrate 4. The AFE 22 includes a capacitor 28b, passives 34a and an AFE integrated circuit (IC) 35. The AFE 22 may be used for signal conditioning. As noted above, the module 1 may include suitable number of AFEs 22. In some embodiments, the AFE 22 may comprise a sensor, such as a volatile organic compounds (VOC) sensor. The sensor may comprise gas, pressure, humidity, and/or temperature sensor(s).

Figure 2F:
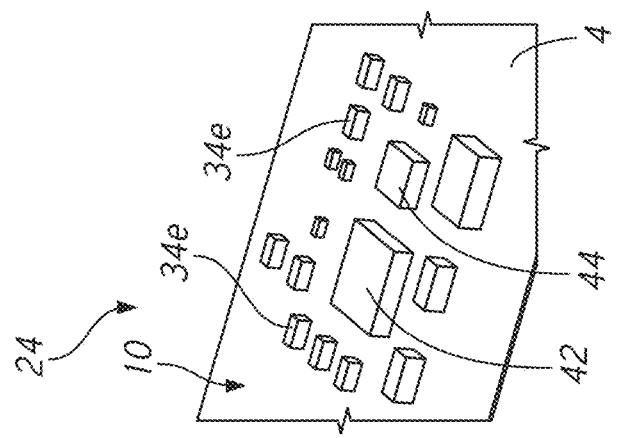
FIG. 2F is a schematic perspective view of power management devices mounted to the first side of the substrate of the sensor module of FIG. 1.
Figure 2E:
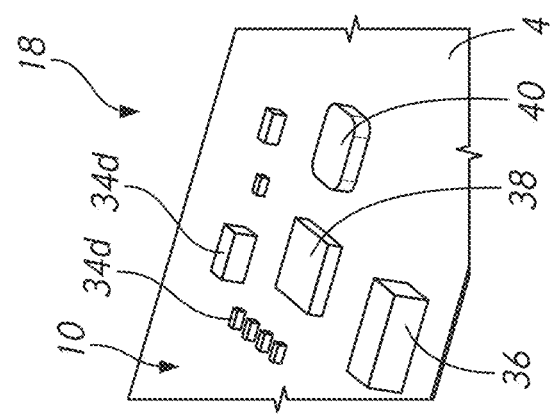
FIG. 2E is a schematic perspective view of an antenna assembly mounted to the first side of the substrate of the sensor module of FIG. 1.
Figure 2D:
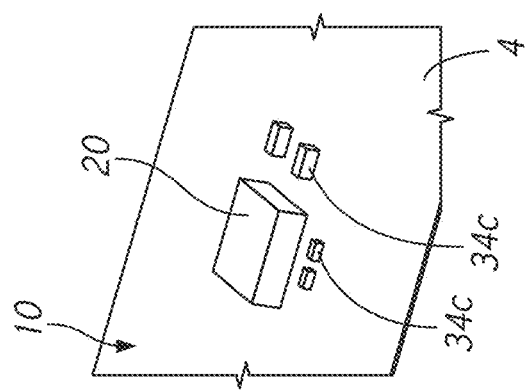
FIG. 2D is a schematic perspective view of an accelerometer mounted to the first side of the substrate of the sensor module of FIG. 1.
Figure 2C:
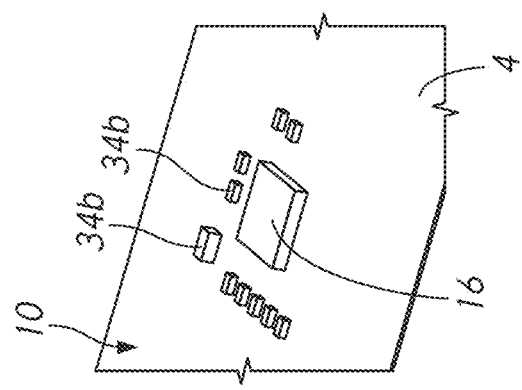
FIG. 2C is a schematic perspective view of a controller mounted to the first side of the substrate of the sensor module of FIG. 1.

FIG. 2C illustrates the microcontroller 16 with passive components 34b mounted to the first side 10 of the substrate 4. FIG. 2D illustrates the accelerometer 20 with passive components 34c mounted to the first side 10 of the substrate 4. FIG. 2E illustrates the antenna assembly 18 mounted to the first side 10 of the substrate 4. The antenna assembly 18 can include passive components 34d, antenna 36, Bluetooth Low Energy (BTLE) radio chip 38, and crystal 40. The antenna assembly 18 may communicate with external computing devices through wireless data communication, in some embodiments. FIG. 2F illustrates the power management devices 24 mounted to the first side 10 of the substrate 4. The power management devices 24 can include passive components 34e, DC-DC buck converter 42, and DC-DC buck booster 44 mounted to the first side 10 of the substrate 4.

In some embodiments, the optical sensor dies (e.g., photodetector 26) of the photometric island 14a, 14b, 14c can transduce biological signals from the user's body, and associated device dies can process the signals. Signals from the accelerometer 20 and other sensors can also be processed by associated processing dies. The processed data can be wirelessly transmitted by the antenna assembly 18 to an external computing device, such as a portable electronic device (e.g., mobile smartphone, tablet computing device), a laptop computer, a central server, etc.

Figure 3:
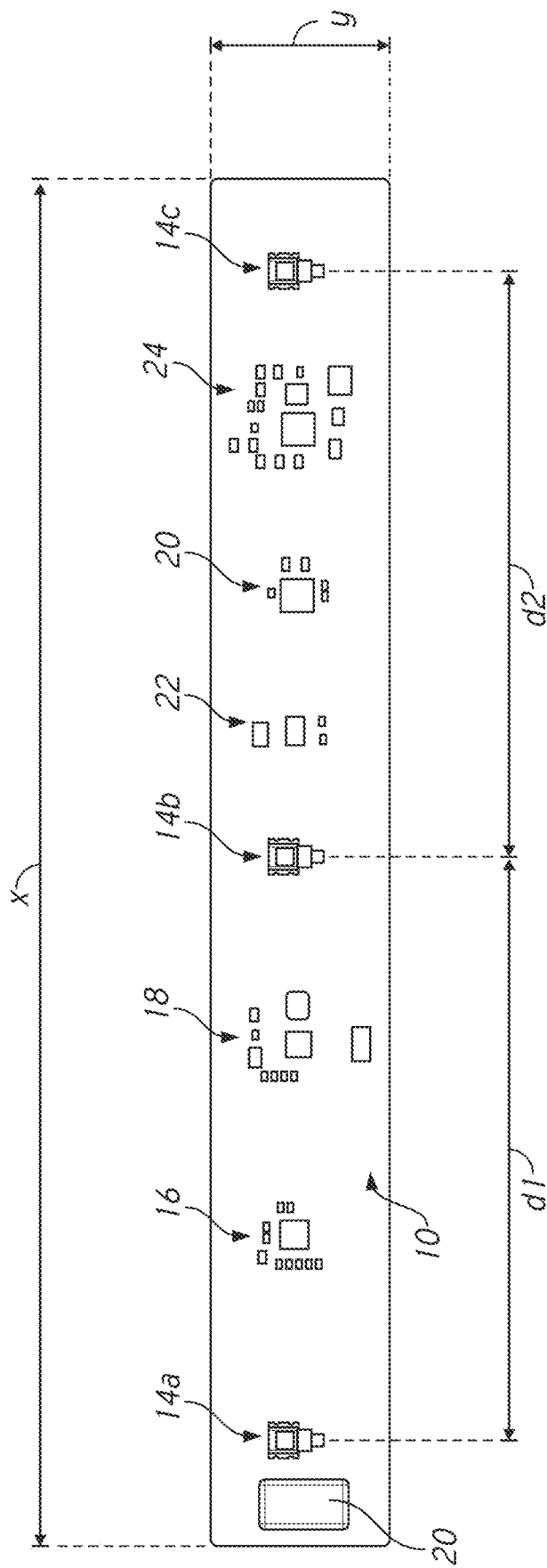
FIG. 3 is a top plan view of the module shown in FIG. 1.

FIG. 3 is a top view of the module 1 in one embodiment. The plurality of integrated device dies disposed on the first side 10 of the substrate 4 may be spaced apart from each other. In some embodiments, the substrate 4 may have an elongate shape to carry the device dies. For example, the substrate shown in FIG. 1 may have a length x, from one end to another along the elongate shape, of about 140 mm (e.g., 100 mm to 200 mm). It should be understood that the length x may vary depend on, for example, the use of the device. The substrate 4 of FIG. 1 may have a width y of about 2 mm (e.g., 0.5 mm to 3.5 mm). As the length x and the width y collectively define an area of the first side 10, measurements of the length x and the width y may depend on each other. In some embodiments, the elongate shape may be suitable for a device, such as, a wristband device, etc. In some embodiments, the substrate 4 may have a flexible radius of about 5 cm (e.g., 3 cm to 7 cm).

Figure 4A:
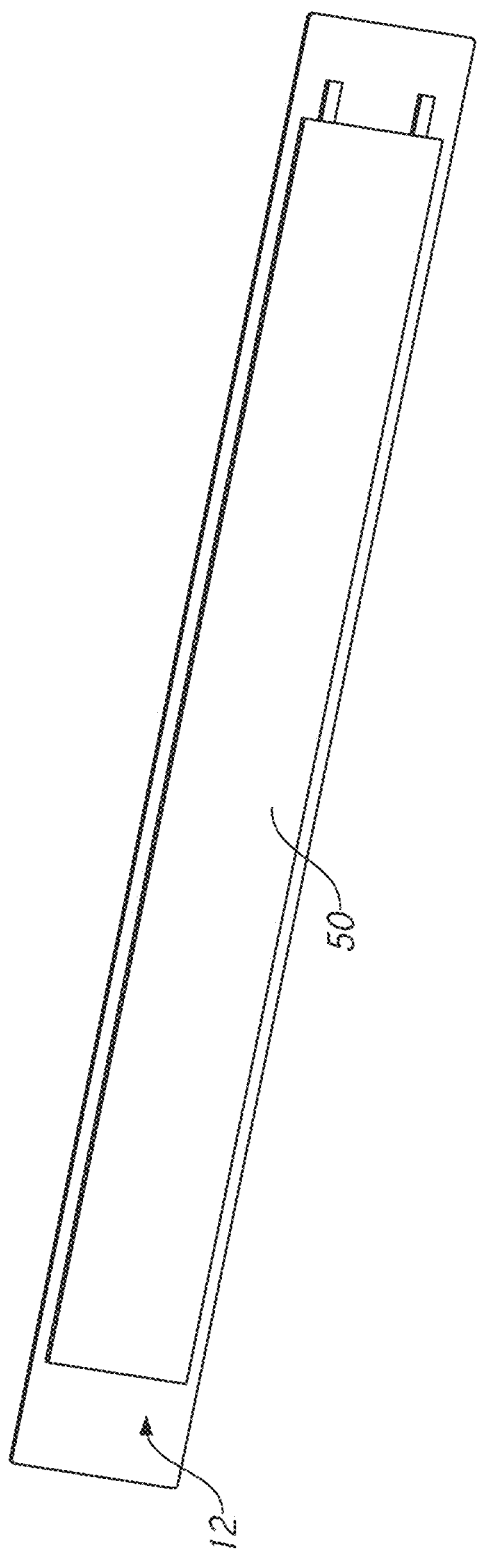
FIG. 4A is a schematic perspective view of a second side of the sensor module according to one embodiment.
Figure 4B:
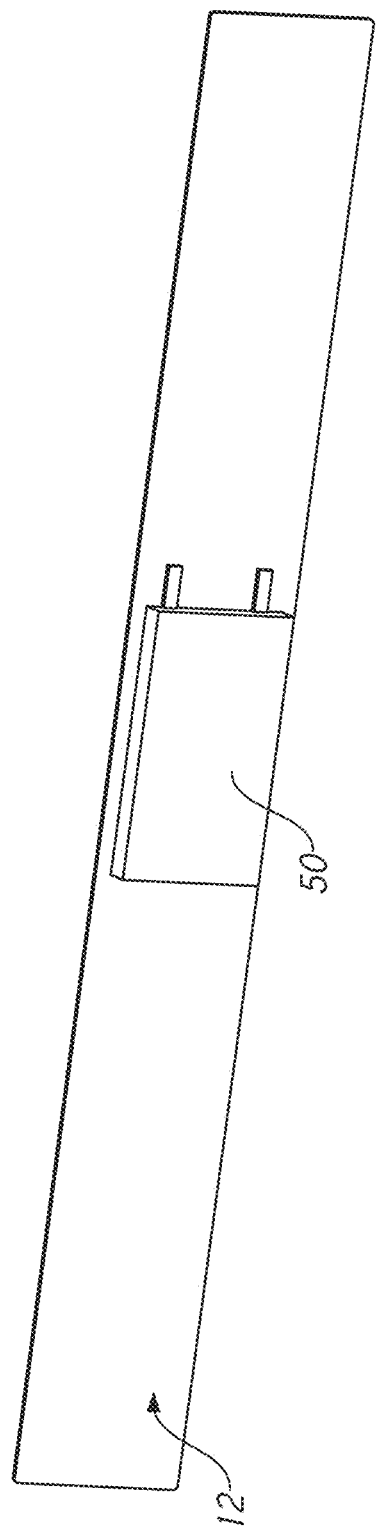
FIG. 4B is a schematic perspective view of a second side of the sensor module according to one embodiment.

FIGS. 4A and 4B show a second side 12 opposite the first side 10 of the sensor module 1, which, in the embodiment of FIGS. 1-7, may face away from the user. As shown in FIGS. 4A and 4B, a battery 50 can be mounted to the second side 12 of the substrate 4 and can electrically communicate with the components on the first side 10 by way of, for example, metallic traces in the substrate. In some embodiments, the battery 50 can comprise a flexible battery configured to bend or flex with the user's movements. As illustrated in FIGS. 4A and 4B, a size of the battery 50 may vary. In some embodiments, a relatively large battery may be more suitable, for example, to enable processing electronics to process signals within the module 1. In some other embodiments, a smaller battery may be more suitable for, for example, reducing the overall size of the module 1. In some embodiments, the battery 50 may comprise multiple battery portions that are electrically connected together. In some embodiments, the module 1 may include more than one battery 50. It should be understood that the battery 50 may be disposed on the first side 10 of the substrate 4, in some embodiments.

Figure 5A:
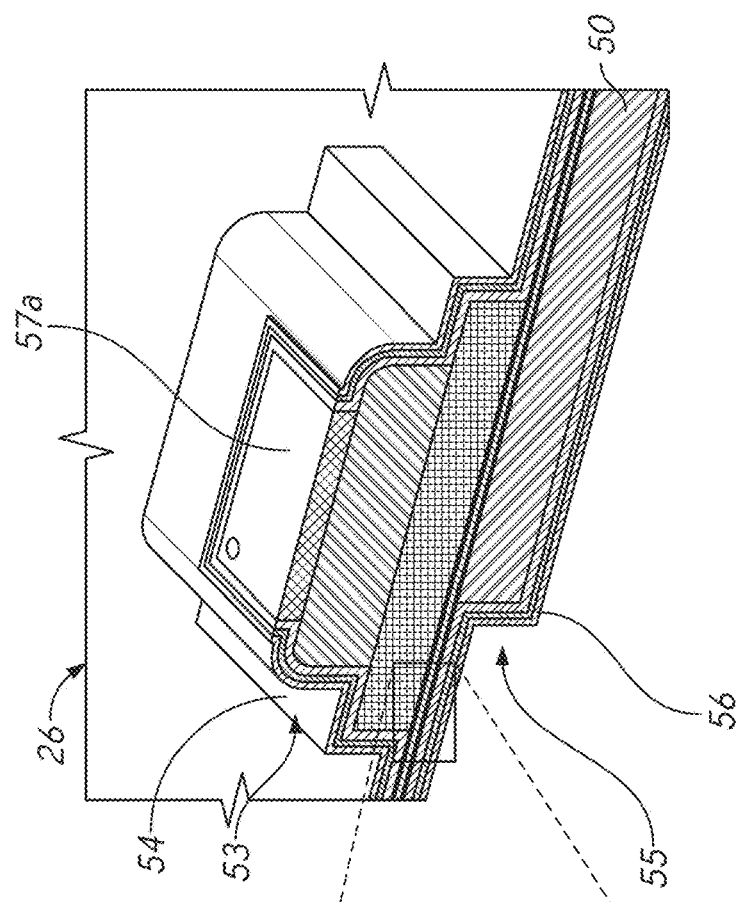
FIG. 5A is a cross sectional view of a photodetector of the photometric island of the module.
Figure 5B:
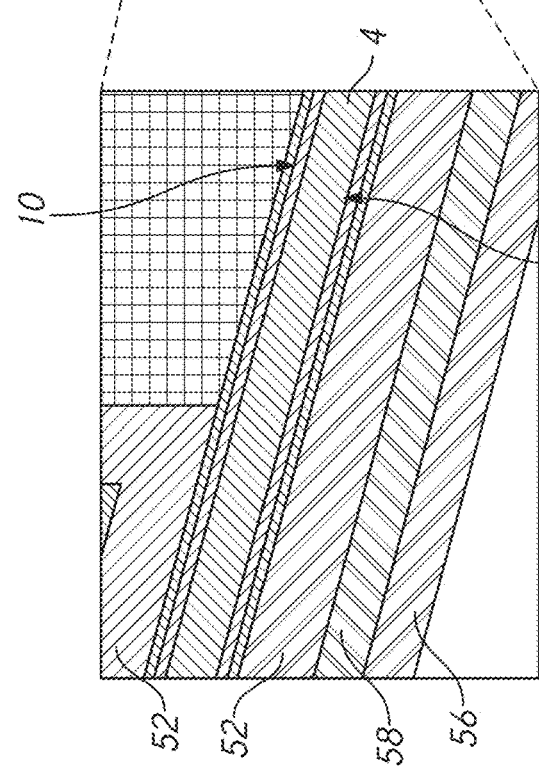
FIG. 5B is a magnified view of the cross section of FIG. 5A showing layers formed thereon.

FIG. 5A is a schematic cross-sectional view of a portion of the sensor module 1 taken along the photodetector 26 of the photometric island 14a shown at least in FIG. 1. FIG. 5B shows a magnified view of layers near the substrate 4 of FIG. 5A. FIG. 6A is a schematic cross-sectional view of a portion the sensor module 1 taken along the LED 30 of the photometric island 14a shown at least in FIG. 1. FIG. 6B shows a magnified view of the layers near the substrate 4 of FIG. 6B. The layers may include a conformal coating 52, a first cover layer 54, a second cover layer 56. The layers may also include adhesive layers 58.

As explained above, it can be important to waterproof the sensor module 1 so as to protect the sensor module 1 from moisture in wet and/or agitating environments, such as a washing machine, swimming pool, etc. As shown in FIGS. 5A-6B, the conformal coating 52 can be applied over the sensor die(s) and over at least a portion of the first side 10 of the substrate 4. In addition, the conformal coating 52 can be applied over at least a portion of the second side 12 of the substrate 4. As shown, the conformal coating 52 can be applied over the entirety of the integrated device dies on the first side 10 of the substrate 4, except for windows 57a, 57b that can be exposed to enable light to pass from the emitter (LED) 30, and to the detector 26 (e.g., photodiode). Moreover, as shown in FIGS. 5A-6B, the conformal coating 52 can be applied to conform over the battery 50 on the second side 12 of the substrate 4. In some embodiments, the sensor module 1 can be employed as disposable units, for example in a hospital context, such that the battery 50 need not be replaced or recharged. Thus, the conformal coating 52 can be provided over sensitive portions of device dies (such as over processor dies like the microcontroller 16 and other components), but can be opened in one or more windows 57 where various components (such as optical device dies) optically communicate with the user or outside environs. In some embodiments, when the conformal coating 52 is transparent against certain wavelengths, conformal coating may be considered as opened, even if the coating 52 is not physically opened. As explained above, the conformal coating 52 can conform to the surface topology of the underlying structures, e.g., the underlying device dies. In the embodiments of FIGS. 5A-6B, the conformal coating 52 can be thinner than the structures (e.g., dies) that it coats. In other embodiments, however, the coating 52 may be as thick as or thicker than the structures that it coats. Further, as shown in FIGS. 5A-6B, the conformal coating 52 can follow the contours of the underlying structures or dies, such that the coating 52 extends along the substrate to a corner at which the die is mounted, extends upwardly along a sidewall of the die, and extends over across the upper surface of the die. Thus, in the embodiments disclosed herein, the underlying structures can cause protrusions or turns in the conformal coating 52.

In some embodiments, the conformal coating 52 can cover a majority of one or both of the first and second sides 10, 12 of the substrate 4. In some embodiments, the conformal coating 52 can cover substantially the entire first and/or second sides 10, 12 of the exposed portions of the substrate 4. In some embodiments, the conformal coating 52 can cover side edges of the substrate 4. The conformal coating 52 can comprise a flexible, curable material that can conform to the surfaces of the components on the first and second sides 10, 12 of the substrate 4. The flexibility of the conformal coating 52 can beneficially enable the sensor module 1 to move with the user's movements. In some embodiments, the conformal coating 52 may be as flexible as, more flexible than, or less flexible than the substrate 4. In some embodiments, for example, the conformal coating 52 can be sprayed onto the first and second sides 10, 12. In some other embodiments, the conformal coating 52 may be applied by dipping the substrate with electrical components into a solution of the conformal coating 52. In some embodiments, the coating 52 can be cured after application, e.g., natural curing, ultraviolet (UV) curing, thermal curing, etc. Beneficially, the conformal coating 52 can comprise a waterproof coating that can prevent moisture or liquids from contacting sensitive components or electrical connections. In various embodiments, the conformal coating 52 can be transparent in some embodiments. For example, the transparent conformal coating 52 may allow light transmitted from the LED 30 and reflected light from the user's body to pass through. The conformal coating 52 can be capable of conformal deposition (e.g., spray coating) prior to curing. In various embodiments, the conformal coating 52 can comprise a polymer. For example, in some embodiments, the conformal coating 52 can comprise Dow Corning® 1-2577 conformal coating, manufactured by Dow Corning Corporation of Midland, Mich. It should be appreciated, however, that the conformal coating 52 can comprise other materials. In addition to being waterproof, the conformal coating 52, along with other protective layers of the device, may be sufficiently durable to withstand at least 50 machine "washes," where "washes" are standard washes as defined by ASME, AATCC, and/or other textile organizations developing a standard for electronic technologies integrated with garments. In some embodiments, the conformal coating 52 may be provided for moisture barrier and a polyolefin layer may be provided for water and/or moisture resistance. In some embodiments, a molded thermoplastic elastomers (TPE) may be provided to for water and/or moisture resistance in place of or in addition to other water and/or moisture resistant layer(s). It should be understood that any other suitable layer(s) and/or cover(s) may be applied or provided in place of or in addition to other water and/or moisture resistant layer(s).

Figure 7:
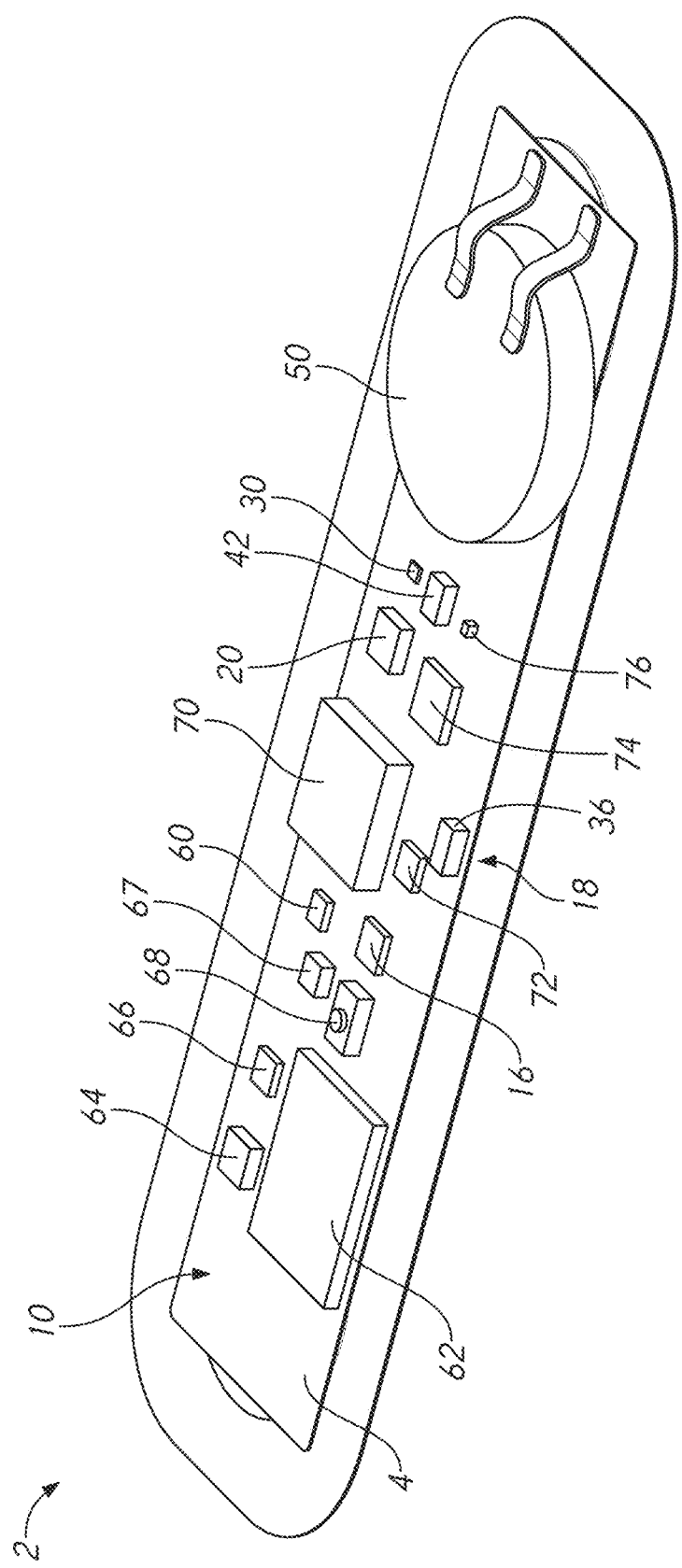
FIG. 7 is a schematic perspective view of a first side of a sensor module according to one embodiment.

Further, a first cover 53 can be provided over the conformal coating 52 on the first side 10, and a second cover 55 can be provided over the conformal coating 52 on the second side 12. The first cover 53 and/or the second cover 55 may be conformally applied over the conformal coating 52 to follow a surface contour and/or a surface topology of the conformal coating 52. In the embodiment of FIGS. 6 and 7, for example, the first and second covers 53, 55 can each comprise respective first and second cover layers 54, 56 (e.g., a foam). The first and second cover layers 54, 56 can attach to the conformal coating 52 by way of an adhesive 58 (e.g., acrylic). The first and second covers 53, 55 can advantageously protect the sensor module components and can improve the waterproofing of the sensor module 1. The first and second cover layers 54, 56 can comprise relatively soft layers (e.g., like cotton, cloth, etc.) which can provide flexibility and comfort to the user. In some embodiments, the first and second cover layers 54, 56 may be as flexible as, more flexible than, or less flexible than the substrate 4. The first and second covers 53, 55 can cooperate with the conformal coating 52 to provide a watertight seal around the sensor module 1. For example, the substrate 4 can be entirely embedded within the conformal coating 52. In some embodiments, the substrate 4 can be entirely embedded within the first and second covers 53, 55.

The sensor module of FIGS. 1-6B can be worn by the user in various embodiments. For example, in some embodiments, the sensor module 1 can be adhered to the user, for example, like a bandage. Tape or other adhesive can be applied to the sensor module 1, and the tape can attach the module 1 to the user. In some embodiments, the sensor module 1 can be disposable, such that the module 1 can be discarded after use. In other embodiments, the sensor module 1 can be used for an extended period of time. In other embodiments, the first and/or second covers 53, 55 can be integrated (e.g., sewn) into a clothing garment worn by the user. In other embodiments, the first and/or second covers 53, 55 can comprise an adhesive configured to be attached to the user for wearing during use. Beneficially, the conformal coating 52 and/or the first and second covers 53, 55 can provide a waterproof enclosure for the sensor module 1.

Turning to FIGS. 7-16C, embodiments of a sensor module 2 comprising electrical sensing devices are disclosed. The sensing devices or sensors can include a sensing electrode and a sensor die configured to process signals transduced or detected by the sensing electrode. For example, the illustrated embodiments can comprise an electrocardiogram (ECG) device that comprises one or a plurality of ECG electrodes or pads 82 on a second side 12 of a substrate 4. One or a plurality of integrated device dies can be mounted to a first side 10 of the substrate 4. In the embodiments of FIGS. 7-16C, therefore, the second side 12 with ECG pads 82 can face the user's body, and the first side 10 with integrated device dies can face away from the user. Unless otherwise noted, the components, materials, and functionality described above in connection with FIGS. 1-6B may be used interchangeably with the embodiment described herein in relation to FIGS. 7-16C. Reference numerals used in conjunction with FIGS. 1-6B may represent the same or generally similar components as those of FIGS. 7-16C, unless otherwise noted. Beneficially, as with the embodiment of FIGS. 1-6B, the embodiment of FIGS. 7-16C can be self-contained so as to provide power (e.g., by way of the battery), sensing, processing, and wireless data communication within the sensor module.

FIG. 7 shows a perspective view of the sensor module 2 according to one embodiment. The sensor module 2 can include a microcontroller 16, a heart rate monitor 60, a memory device 62, a regulator 64, an analog-to-digital converter 66, a diode 67, a button 68 for controlling the operation of the module, an indicator 70 (e.g., beeper), an antenna assembly 18, a radio frequency (RF) transceiver 72, a temperature (T) sensor 74, a power switch 76, a motion sensor (e.g., accelerometer 20), an LED 30, a DC-DC converter 42, and a battery 50 mounted to the first side 10 of the substrate 4. Two or more of these components may be electrically connected to transfer signals, for example, by way of traces embedded in the substrate 4. In some embodiments, the user may control certain functions (e.g., start, end, power-on, power-off, etc.) by pressing the button 68. In some embodiments, the indicator 70 may indicate, for example, an operation status of the module 2.

Figure 8:
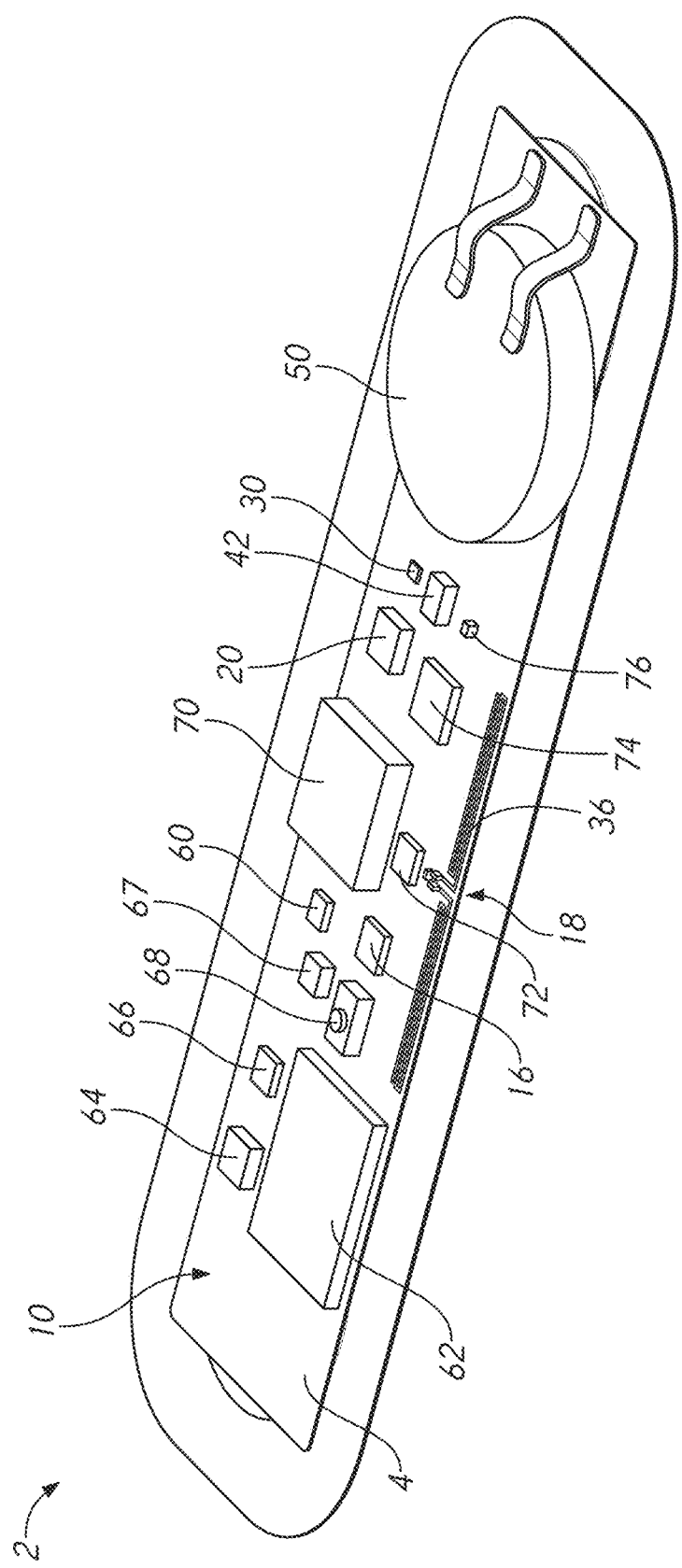
FIG. 8 is a schematic perspective view of a first side of a sensor module according to one embodiment with an antenna printed on a substrate.

FIG. 8 shows a perspective view of the sensor module 2 according to one embodiment. While the antenna assembly 18 of FIG. 7 comprises a chip antenna 36 (e.g., an antenna die), the antenna assembly 18 of FIG. 8 comprises an antenna 36 printed on the substrate 4. The antenna 36 can be printed or otherwise patterned onto the substrate 4. However, any other suitable types of antenna may be used for the antenna assembly 18. The antenna assembly 18 can be configured to provide wireless data communication with external devices.

Figure 9A:
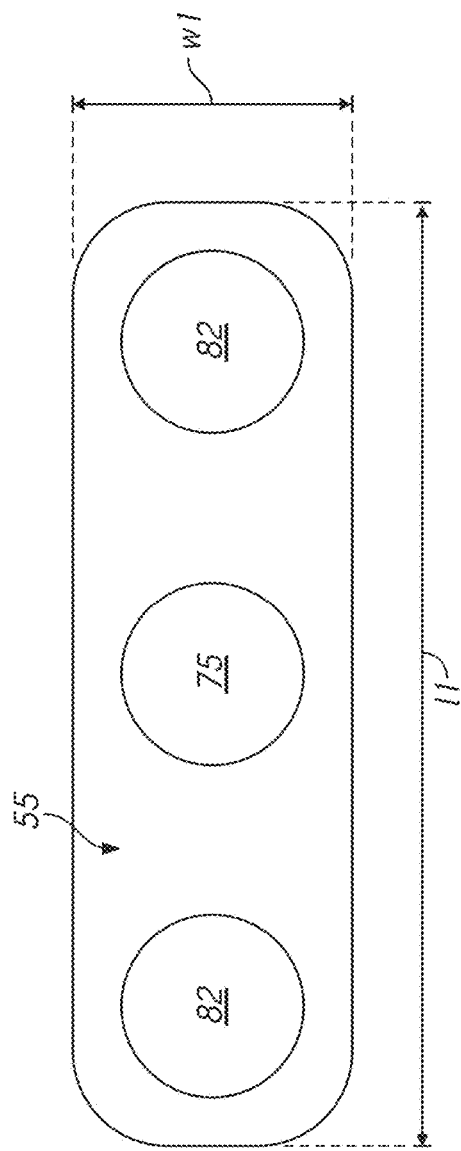
FIG. 9A is a second side plan view of the module of FIGS. 7 and/or 8.
Figure 9B:
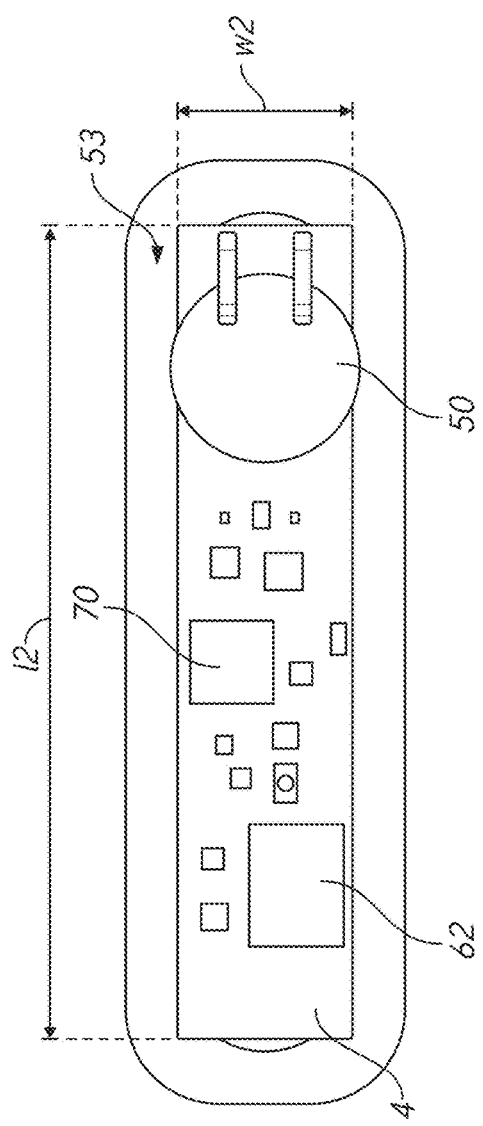
FIG. 9B is a first side plan view of the module of FIGS. 7 and/or 8.

FIG. 9A shows a plan view of the second side 12 of the sensor module 2 in one embodiment. FIG. 9B shows a plan view of the first side 10 of the sensor module 2 in one embodiment. The module 2 can include the ECG pads 82 on the second side 12 of the substrate 4 that can be configured to contact the user's skin, e.g., by way of a conductive gel and/or conductive cloth patches or other intervening material in some embodiments. During use, the ECG electrodes or pads 82 can transduce electrical signals associated with the user's heart (or other source of electrical signals). The signals can be transferred through, for example, traces in the substrate to the integrated device dies on the first side 10 of the substrate 4. In various embodiments, a sensor die (e.g., heart monitor sensing die) on the first side 10 can process the signals transduced by the ECG electrode or pad 82. The processed signals can be transmitted wirelessly to an external computing device, such as a mobile electronic device (e.g., smartphone, tablet computing device, etc.), a laptop computer, a central server, etc. In some embodiments, the module 2 can also include a temperature sensor pad 75 that is configured to measure the user's body temperature, or any other types of sensors or pads.

The module 2 may have a length l1 along a longitudinal axis and a width w1 along a transverse axis perpendicular to the longitudinal axis. In some embodiments, the length l1 of the module 2 may be, for example, about 10 cm (e.g., 5 cm to 15 cm). In some embodiments, the width w1 of the module 2 may be, for example, about 3 cm (e.g., 2 cm to 4 cm). The substrate 4 of the module 2 may have a length l2 along the longitudinal axis and a width w2 along the transverse axis. The length l2 of the substrate 4 may be, for example, about 8.5 cm (e.g., 4.5 cm to 14.5 cm). The width w2 of the substrate 4 may be, for example, about 2 cm (e.g., 1 cm to 3 cm).

Figure 10:
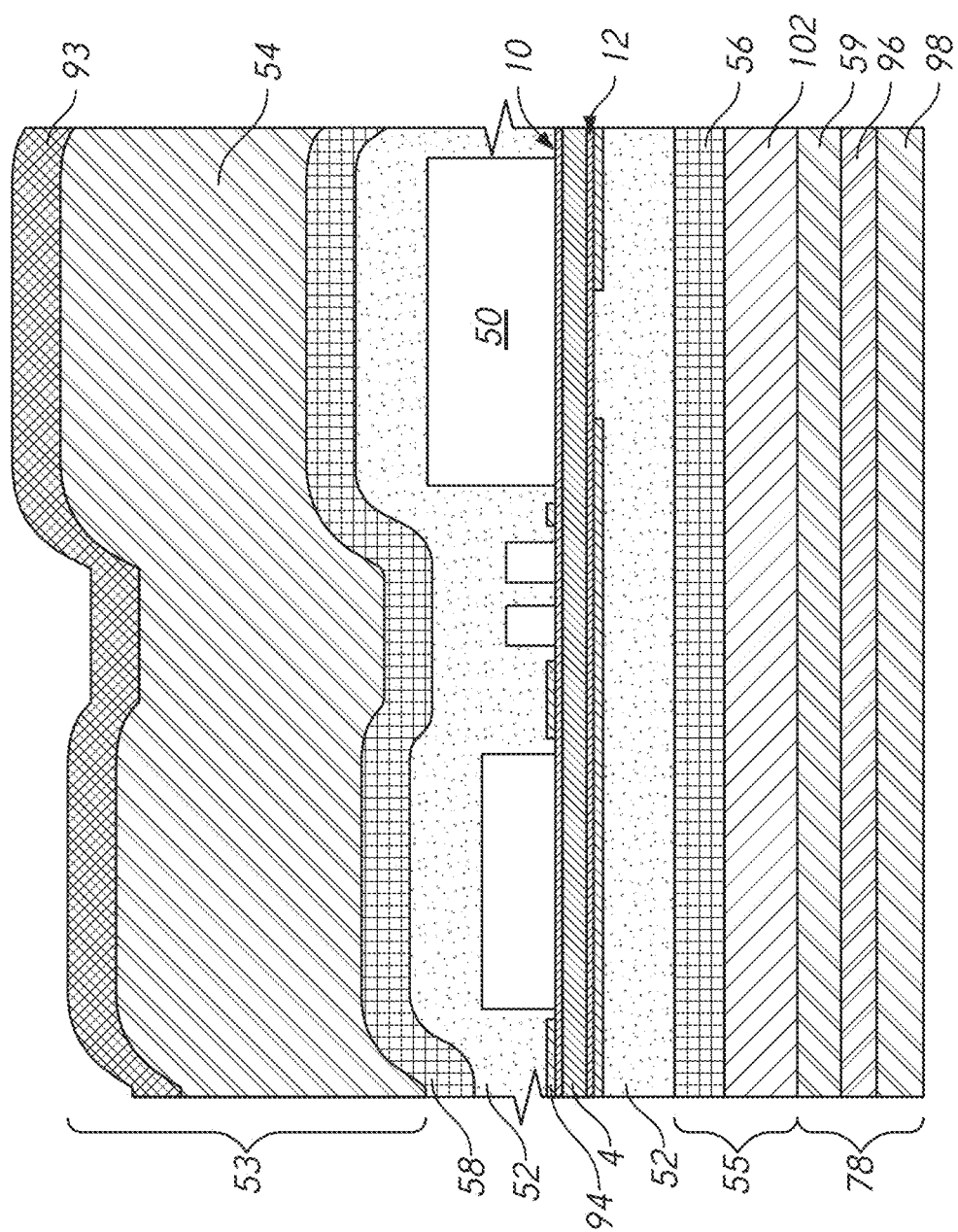
FIG. 10 is a cross-sectional view of a portion of the module showing layers formed thereof.

FIG. 10 illustrates a cross-sectional view of a portion of the module 2 showing layers formed thereof, according to one embodiment. The layers illustrated in FIG. 10 include a first cover 53, an adhesive layer 58, a conformal coating 52, a solder mask layer 94, a second cover 55, and a tape 78 (e.g., a double sided tape). The first cover 53 may comprise a first cover layer 54 (e.g., a foam material such as SCF®) and a protective layer 93 (e.g., white polyethylene terephthalate (PET)). The second cover 55 may comprise a second cover layer 56 (e.g., a conductive adhesive) and a conductive cloth 102. The tape 78 may comprise an adhesive 59, a carrier 96, and a gel 98. In other embodiments, however, the tape 78 may comprise a single layer. In some embodiments, the tape 78 can be used to adhere the sensor module to the user's body. Beneficially, the embodiment shown in FIG. 10 can provide a waterproof package for the electronics of the module 2. In some embodiments, the conformality of each layer may vary (e.g., one of the layers may be more conformal than other layers).

FIG. 11A shows a cross-sectional view of a portion of the module 2 of, for example, FIG. 7 or 8) near the battery 50 and the electrode pad 82. The illustrated embodiment of FIG. 11A includes a coin or button battery. However, the module 2 may include any form of battery. FIG. 11B illustrates a magnified view of FIG. 11A near an edge of the battery 50 and the ECG pad 82, showing layers formed thereof. As illustrated, the ECG pad 82 is disposed on the second side 12 of the substrate 4, and between the substrate 4 and the conductive cloth 102.

FIG. 11C shows a magnified view of a portion of the layers formed on the substrate 4 illustrated in FIG. 11B. The layers may include the conformal coating 52 and the adhesive layers 58 on the first and second side 10, 12 of the substrate 4. The adhesive layer 58 may adhere the first cover layer 54 on the first side 10. The adhesive layer 58 may adhere the carrier 96, the gel 98 and a liner 100 on the second side 12.

FIG. 11D shows a connection between the ECG pad 82 and the substrate 4 in one embodiment. As illustrated in FIG. 11D, in some embodiments, the ECG pad 82 may be electrically connected to the substrate 4 through a via 104 (e.g., a through substrate via (TSV)). In some embodiments, the substrate 4 may comprise a conductive layer formed therein. The ECG 82 may be connected to the substrate 4 with a conductive material 106 (e.g., a conductive epoxy, solder, etc.) The conductive cloth 102 can allow for electrical communication between the ECG pad 82 and the user's body, while providing a waterproof property. In some embodiments, the conformal coating 52 or any other layers may be disposed between the conductive cloth 102 and the substrate 4.

Figure 11:
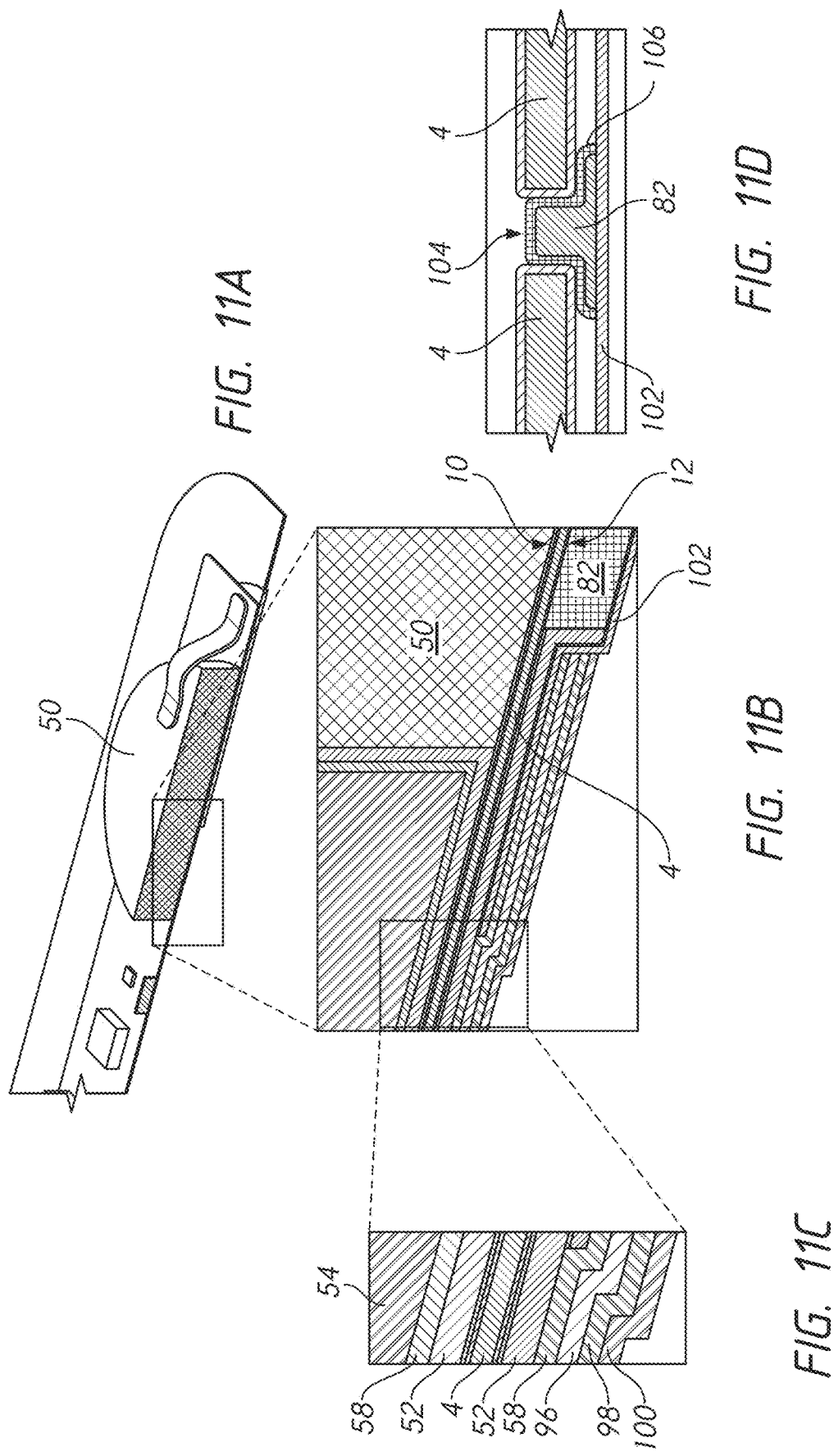
FIG. 11A is a cross-sectional view of a portion of the module near a battery and an electrode pad.
FIG. 11B is a closer view of FIG. 11A near an edge of the battery and the electrode pad, showing layers formed thereon.
FIG. 11C is a closer view of a portion of the layers formed on the substrate illustrated in FIG. 11B.
FIG. 11D shows a connection between the electrode pad and the substrate in one embodiment.

It can be important to waterproof the sensor module of FIGS. 7-15B, as explained above. As shown in FIGS. 10-11D, the conformal coating 52 can be applied over the surfaces of the integrated device dies (e.g., including the sensor die(s)), at least a portion of the first side 10 of the substrate 4, and at least a portion of the second side 12 of the substrate 4. As shown, the conformal coating 52 can be applied over the entirety of the integrated device dies (e.g., the microcontroller 16, the heart rate monitor 60, the memory device 62, the regulator 64, the analog-to-digital converter 66, the button 68, the indicator 70, the antenna assembly 18, the RF transceiver 72, the T sensor 74, the power switch 76, the accelerometer 20, the LED 30, and the DC-DC converter 42), the battery 50, and the antenna assembly 18 on the first side 10 of the substrate 4. The module 2 can be configured with a battery charge coil 90 (see FIG. 12) for wirelessly recharging the battery 50 to obviate access to the battery 50 beneath the waterproof coating. Moreover, as shown in FIGS. 9A and 13A, the conformal coating 52 can be applied to conform over the second side 12 of the substrate 4, except for windows that can be provided to expose the electrodes 82 to the user's body. Thus, the conformal coating 52 can be provided over sensitive portions of device dies (such as over processor dies like the microcontroller 16 and other components), but can be opened in one or more windows where various components (such as the ECG electrodes or pads 82) electrically communicate with the user or outside environs.

Figure 12:
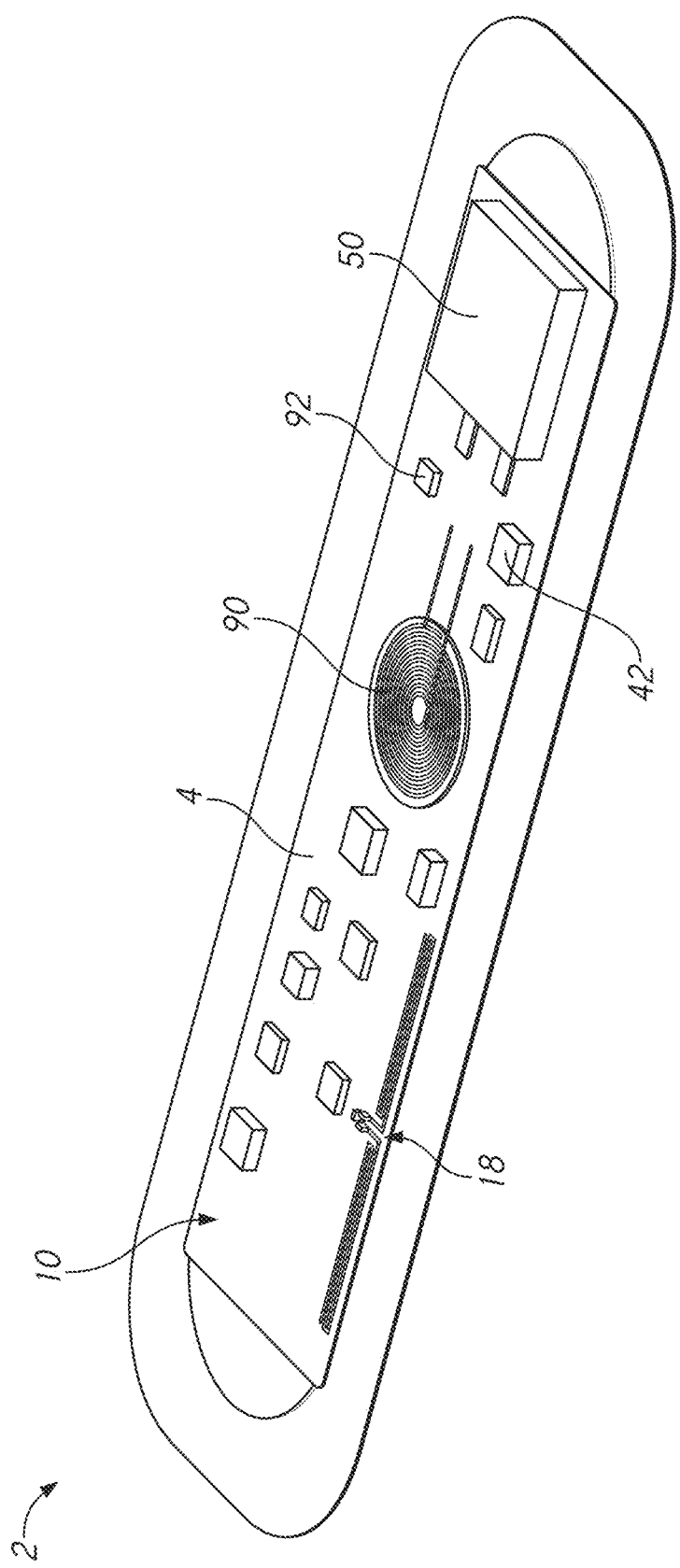
FIG. 12 is a schematic perspective view of a first side of a sensor module according to one embodiment with a battery charging coil.

FIG. 12 is a schematic perspective view of a sensor module 2 according to one embodiment. The module 2 illustrated in FIG. 12 includes the battery charge coil 90. The battery charge coil 90 may wirelessly recharge the battery 50. The battery charging coil 90 may obviate access to the battery 50 beneath the waterproof coating. This may be beneficial as removal and/or re-seal of the waterproof coating for battery charging may be difficult and/or cause imperfect sealing after re-seal. In some embodiments, the battery charging coil 90 may be electrically connected to the battery 50 by way of, for example, traces embedded in the substrate 4. It should be understood that the battery charge coil 90 may be used with any embodiments disclosed herein.

Figure 13A:
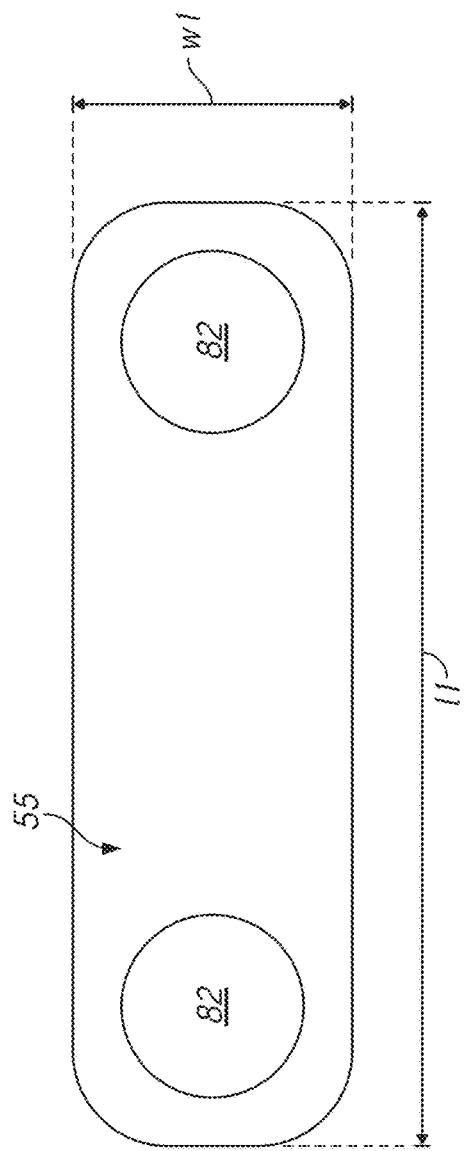
FIG. 13A is a second side plan view of the module of FIG. 12.

FIG. 13A shows the second side 12 of the module 2 shown in FIG. 12. The module 2 includes two ECG pads 82. However, the module 2 may include any number of the pads 82. In some embodiments, the module 2 may also include a temperature pad on the second side 12. The module 2 may have a length l1 along a longitudinal axis and a width w1 along a transverse axis perpendicular to the longitudinal axis. The length l1 and the width w1 of FIG. 13A may be generally similar to the length l1 and the width w1 of the embodiment shown in FIG. 9A. In some embodiments, the length l1 of the module 2 may be, for example, about 10 cm (e.g., 5 cm to 15 cm). In some embodiments, the width w1 of the module 2 may be, for example, about 3 cm (e.g., 2 cm to 4 cm).

Figure 13B:
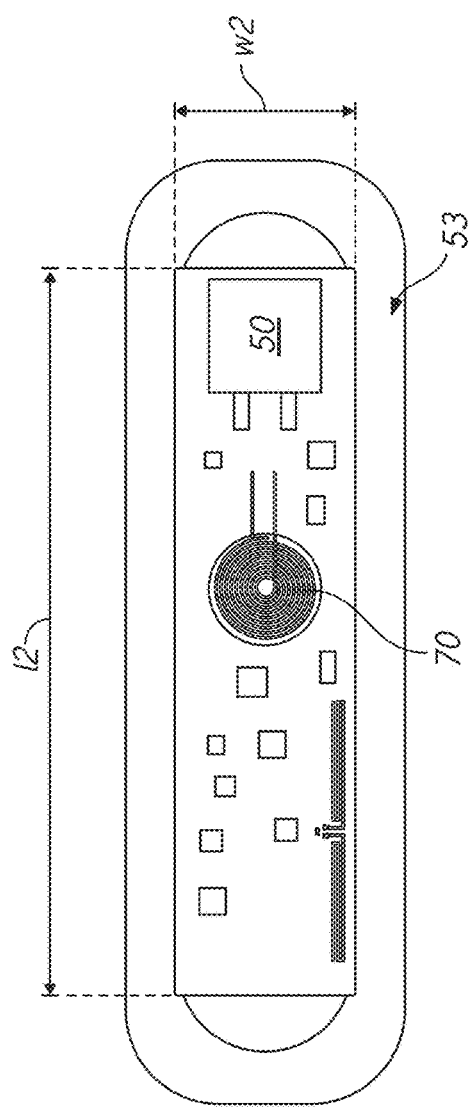
FIG. 13B is a first side plan view of the module of FIG. 12.
Figure 15:
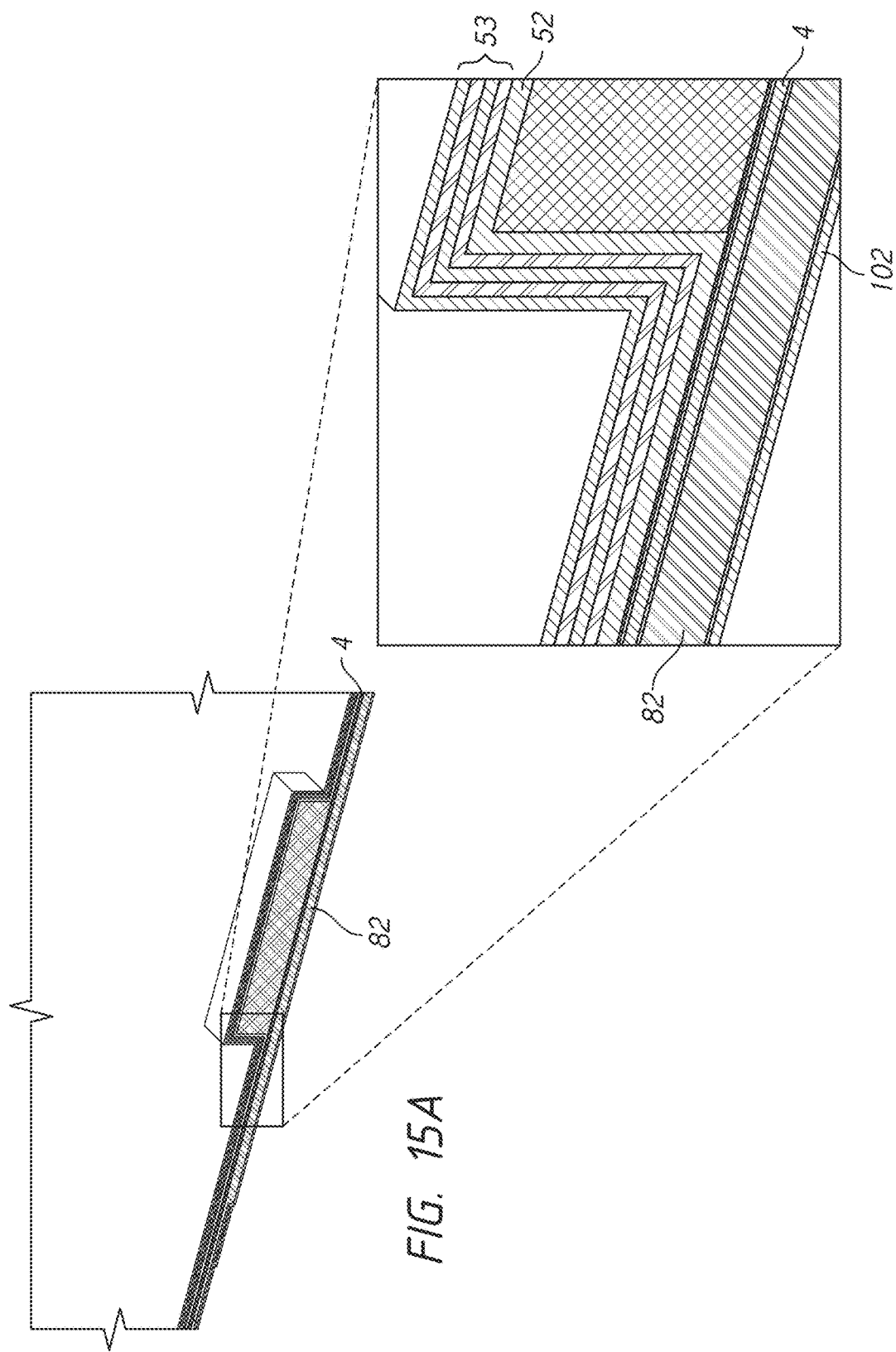
FIG. 15A is a cross sectional view of a portion of the module near a die on the first side and the electrode pad on the second side.
FIG. 15B is a magnified view of FIG. 15A near an edge of the die on the first side.
Figure 16:
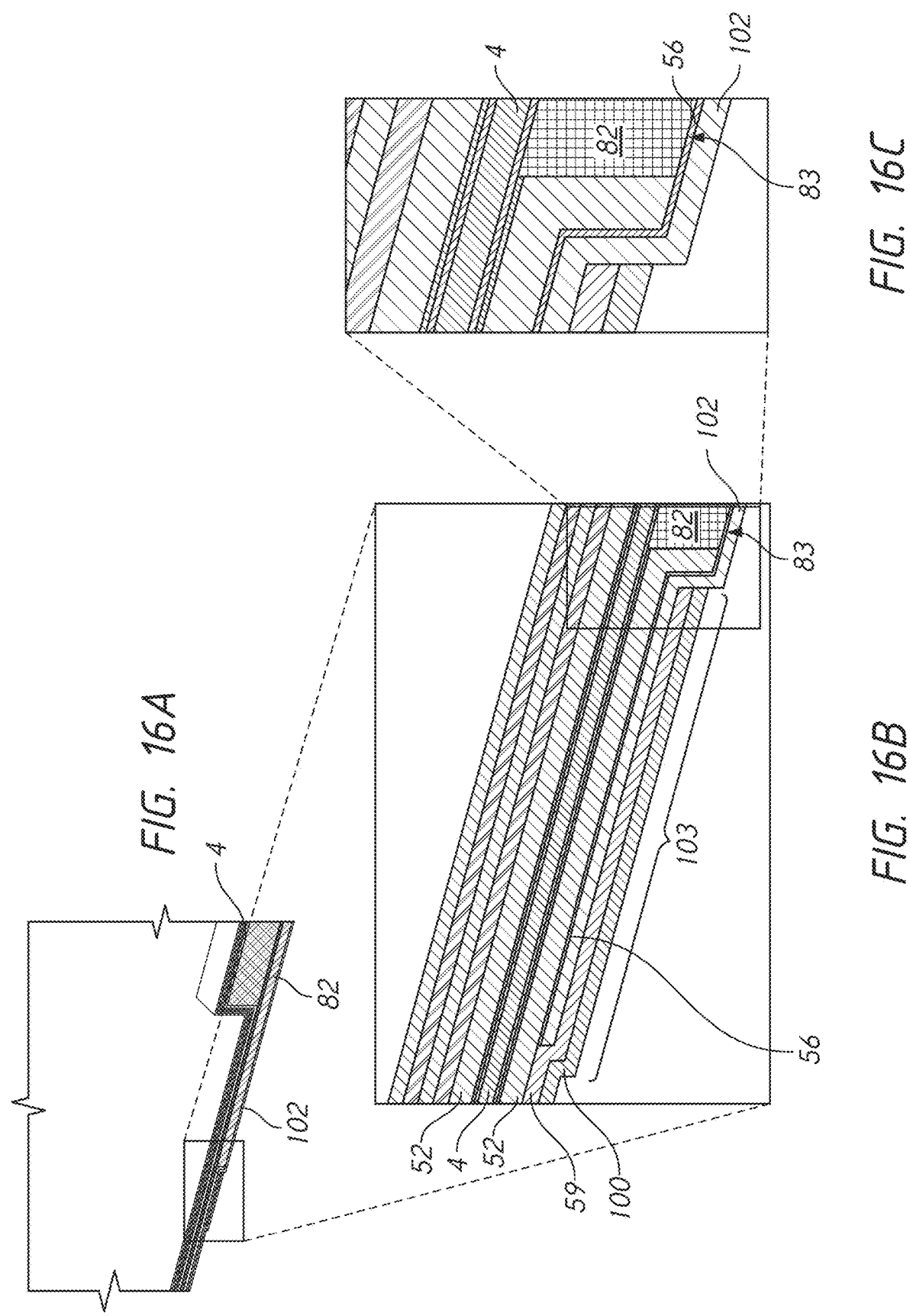
FIG. 16A is a cross sectional view of a portion of the module near an edge of a conductive cloth formed on the second side of the substrate.
FIG. 16B is a magnified view of the portion of the module illustrated in FIG. 16A.
FIG. 16C is a magnified view of the portion of the module illustrated in FIG. 16B.

FIG. 13B is a top plan view of the first side 10 of the module 2 shown in FIG. 12. The substrate 4 of the module 2 may have a length l2 along the longitudinal axis and a width w2 along the transverse axis. The length l2 and the width w2 of FIG. 13B may be generally similar to the length l2 and the width w2 of the embodiment shown in FIG. 9B. The length l2 of the substrate 4 may be, for example, about 8.5 cm (e.g., 4.5 cm to 14.5 cm). The width w2 of substrate 4 may be, for example, about 2 cm (e.g., 1 cm to 3 cm).

FIG. 14 is a table that lists example thickness values for various layers of the sensor module 2. The total thickness shown in FIG. 14 does not include the components mounted on the substrate 4. In some embodiments, a flex core (e.g., polyimide, or PI), top copper (Cu) and a bottom Cu on the list may collectively define the substrate 4. A top and bottom solder resist (SR) layer may comprise the solder mask layers 94 on the first side 10 and the second side 12 as illustrated in, for example, FIG. 10. A conductive adhesive and a conductive cloth on the list may correspond to the second cover layer 56 and the conductive cloth 102 that collectively form the second cover 55 in, for example, FIG. 10. A top release liner, an adhesive and a top close listed on the first three rows of the list may collectively form the first cover 53 of, for example, FIG. 10. A bottom cloth of the list may comprise the liner 100 shown, for example, in FIG. 11C. Beneficially, the layers disclosed herein can provide a waterproof package for the module 2, while maintaining a low profile and thickness. In some embodiments, the thickness for a conformal layer may vary at different locations. For example, the layer may have a greater thickness at a flat portion than at sloped portions of a layer surface. In various embodiments, the conformal coating 52 may be as thick as, thinner than, or thicker than a component mounted on the substrate 4 (such as a device die).

FIG. 15A shows a cross sectional view of a portion of the module 2. The portion of the module 2 shown in FIG. 15A includes one of the dies (e.g., the microcontroller 16, the regulator 64, the analog-to-digital converter, etc. shown in at least FIGS. 7 and 8) on the first side 10 of the substrate 4 and the ECG pad 82 on the second side 12 of the substrate 4. FIG. 15B is a closer view of FIG. 15A near an edge of the die on the first side 10. FIG. 15B shows the edge of the die and the ECG pad 82. The first side 10 includes the conformal coating 52 and the first cover 53 that may comprise a multilayer laminate structure including, e.g., a liner, adhesive layers, and a cloth. The second side 12 may include the ECG pad 82 and the conductive cloth 102.

FIG. 16A shows a cross sectional view of a portion of the module 2 taken near an edge of the conductive cloth 102 formed on the second side 12 of the substrate 4. FIG. 16B is a magnified view of the portion of the module 2 illustrated in FIG. 16A. As illustrated, the conductive cloth 102 covers at least a portion of the bottom surface 83 of the ECG pad 82 and extends from the ECG pad 82. An extended portion 103 of the conductive cloth 102 may be disposed between the conformal coating 52 and the adhesive 59 and liner 100. In some embodiments, the liner 100 can be adhered by the adhesive 59 which is partially adhered to the conformal coating 52 and partially attached to the conductive cloth 102, as shown in FIG. 16B. FIG. 16C shows a magnified view of FIG. 16B at the edge of the ECG pad 82. The conductive cloth 102 may be adhered to the bottom surface 83 of the ECG pad 82 by the conductive adhesive 56. The conductive cloth 102 can provide a soft, conductive surface over the ECG pad 82.

In some embodiments, the conformal coating 52 can cover a majority of one or both of the first and second sides 10, 12 of the substrate 4. In some embodiments, the conformal coating 52 can cover substantially the entire first and/or second sides 10, 12 of the exposed portions of the substrate 4. In some embodiments, the conformal coating 52 can cover side edges of the substrate 4. The conformal coating 52 can comprise a flexible, curable material that can conform to the surfaces of the components on the first and second sides 10, 12 of the substrate 4. The flexibility of the conformal coating 52 can beneficially enable the sensor module 1, 2 to move with the user's movements. In some embodiments, for example, the conformal coating 52 can be sprayed onto the first and second sides 10, 12. In some embodiments, the coating 52 can be cured after application, e.g., natural curing, ultraviolet (UV) curing, thermal curing, etc. Beneficially, the conformal coating 52 can comprise a waterproof coating that can prevent moisture or liquids from contacting sensitive components or electrical connections. In various embodiments, the conformal coating 52 can be transparent in some embodiments. The conformal coating 52 can be capable of conformal deposition (e.g., spray coating) prior to curing. In some embodiments, the conformal coating 52 can comprise Dow Corning® 1-2577 conformal coating, manufactured by Dow Corning Corporation of Midland, Mich. It should be appreciated, however, that the conformal coating 52 can comprise other materials. In addition to being waterproof, the conformal coating, along with other protective layers of the device, should be sufficiently durable to withstand at least 50 machine "washes," where "washes" are standard washes as defined by ASME, AATCC, and/or other textile organizations developing a standard for electronic technologies integrated with garments.

Further, as disclosed herein, a first cover 53 can be provided over the conformal coating 52 on the first side 10, and a second cover 55 can be provided over the conformal coating 52 on the second side 12. As shown in, e.g., FIGS. 9A, 9B, 13A and 13B, the first and second covers 53, 55 can be attached or otherwise connected to one another around the periphery of the substrate 4. The first and second covers 53, 55 can therefore enclose or embed the substrate 4 and moisture-sensitive surfaces to provide a watertight sensor module 1, 2. In various embodiments, for example, the first cover 53 can comprise a first cover layer 54 (e.g., a foam, cotton, cloth, etc.) as shown at least in FIG. 10. A protective layer, such as Polyethylene Terephthalate (PET), can be applied over the first cover layer 54 to provide additional protection and/or waterproofing to the sensor module. The first cover layer 54 can attach to the conformal coating 52 by way of an adhesive (e.g., acrylic). Beneficially, the first cover 53 can be sufficiently flexible so as to move with the user. Moreover, the first cover layer 54 can be soft to improve the comfort to the user of wearing the sensor module 2.

The second cover 55 can comprise a cloth material (including, e.g., conductive cloth patches) adhered to the conformal coating 52, as shown at least in FIG. 10, by way of an adhesive (e.g., a conductive adhesive). A double-sided tape can be applied over the cloth; for example, in some embodiments, the double-sided adhesive can be used to adhere the sensor module to the user's body. In other embodiments, however, the first and/or second covers 53, 55 can be integrated (e.g., sewn) to the user's garments.

The first and second covers 53, 55 can advantageously protect the sensor module components and can improve the waterproofing of the sensor module 1, 2 disclosed herein. The first and second cover layers 54, 56 can comprise relatively soft layers (e.g., like cotton, cloth, etc.) which can provide flexibility and comfort to the user. The first and second covers 53, 55 can cooperate with the conformal coating 52 to provide a watertight seal around the sensor module 1, 2. For example, the substrate 4 can be entirely embedded within the conformal coating 52. In some embodiments, the substrate 4 can be entirely embedded within the first and second covers 53, 55. Furthermore, the cloth covers facilitate integration, such as by sewing, the sensor module into garments. As seen in FIGS. 15A-16C, the cloth covers 53, 55 extend beyond the flexible substrate 4 such that they can be sewn into or otherwise integrated with other textiles that form garments. For example, the sensor module 1, 2 can be integrated into portions of the garment that fit tightly about a portion of the user's anatomy from which biometric signals can be readily obtained (e.g., about the user's chest, arm, wrist, leg, etc.). In various embodiments, as explained with respect to FIG. 10, a white PET layer may be disposed over a foam or SCF layer, which can be adhered to the conformal coating 52 by an adhesive. The conformal coating 52 can be applied over a solder mask layer 94 on the substrate 4, which can comprise a core with metallic (copper) layers on top and bottom, with another solder mask layer 94 below. The conformal coating 52 on the bottom can be applied over the second solder mask layer 94, and a conductive adhesive can be disposed on the conformal coating 52. A conductive adhesive can adhere the conductive cloth 102 to the conformal coating 52. A double sided tape 78 can be provided on the conductive cloth 102. The double sided tape 78 can comprise an adhesive attached to the conductive cloth, a carrier, and a gel.

Thus, the embodiments disclosed herein can provide a waterproof or watertight coating conformally applied over the dies and both sides of the substrate 4. The coating and covers can be flexible and soft so as to improve the movability and comfort of the sensor module 1, 2. Moreover, as explained herein, the sensor module 1, 2 can comprise a self-contained assembly in which biological signals can be sensed, processed, and wirelessly transmitted to external computing devices, and can be powered by one or more on-board batteries.

Figure 17:
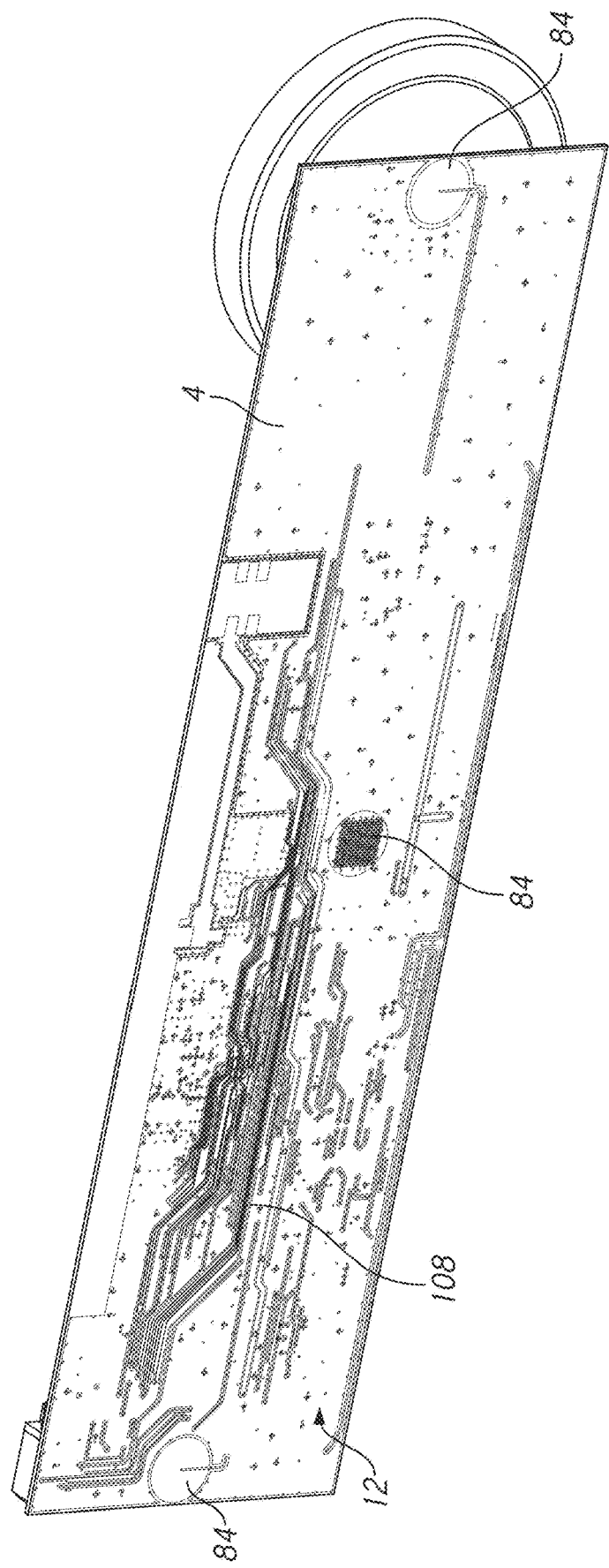
FIG. 17 is a perspective view of the second side of the substrate of FIGS. 7 and/or 8.

FIG. 17 shows the second side 12 of the substrate 4 of the module 2 illustrated, for example, in FIGS. 7 and 8. The second surface 12 of the substrate 4 can comprise contacts 84 where one or more electrode pads (e.g., the ECG pads 82 shown in FIG. 9A) may be attached. In some embodiments, the contact 84 may be used for a temperature sensor pad. For example, in the embodiment illustrated in FIG. 9A, two ECG pads may be connected to the contacts 84 at two edges of the substrate 4 and a temperature sensor pad may be connected to the contact 84 at the middle of the substrate 4. The substrate 4 can have traces 108 configured to electrically connect one or more components mounted to the substrate 4.

Figure 18:
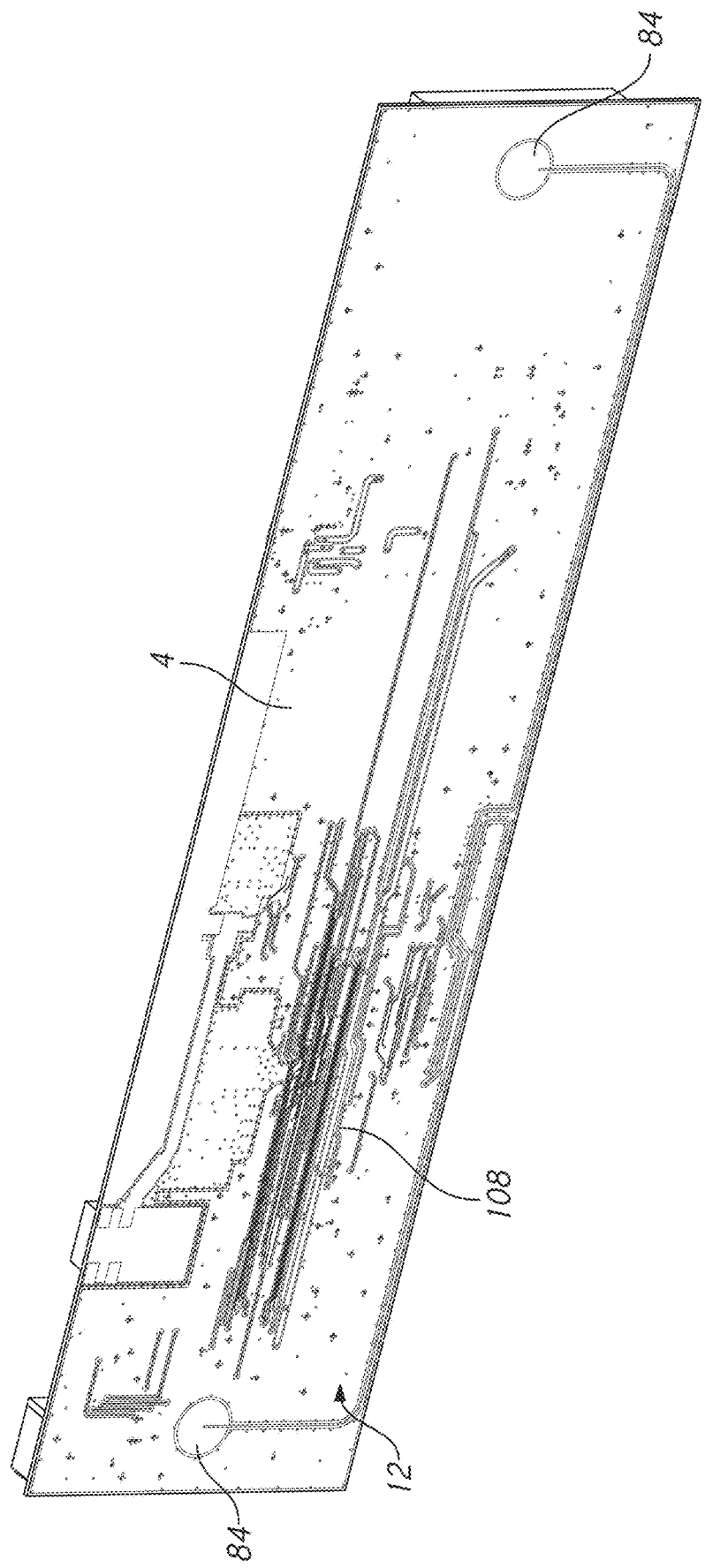
FIG. 18 is a perspective view of the second side of the substrate of FIG. 12.

FIG. 18 shows the second side 12 of the substrate 4 of the module 2 illustrated, for example, in FIG. 12. The second surface 12 of the substrate 4 can comprise contacts 84 where one or more electrode pads (e.g., the ECG pads 82 shown in FIG. 13A) may be provided. In some embodiments, the contact 84 may be used for a temperature sensor pad. For example, in the embodiment illustrated in FIG. 13A, two ECG pads may be connected to the contacts 84. The substrate 4 can have traces 108 configured to electrically connect one or more components mounted to or connected to the substrate 4.

Figure 19A:
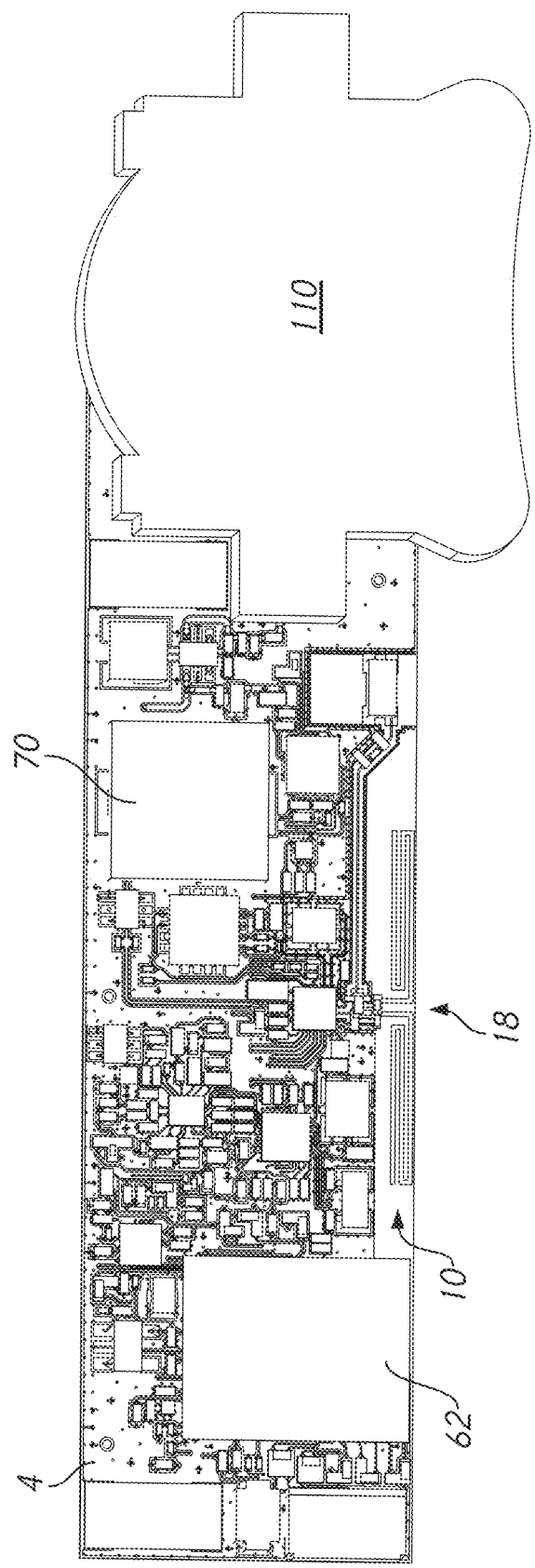
FIG. 19A is a top plan view of a sensor module with a battery holder according to one embodiment.
Figure 19B:
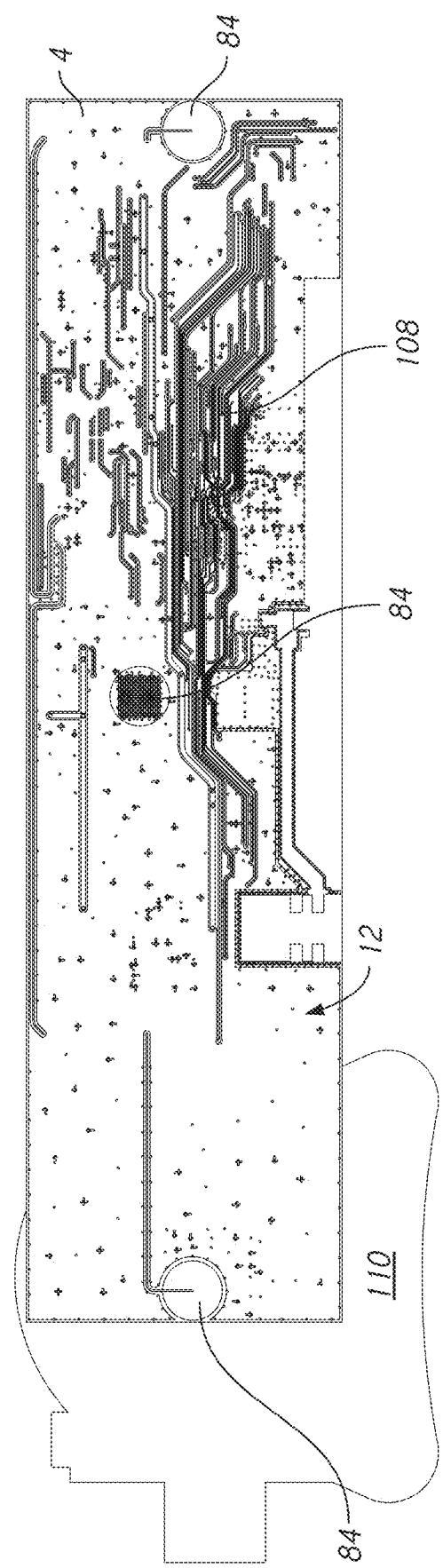
FIG. 19B is a bottom plan view of the sensor module shown in FIG. 19A.

FIG. 19A shows a schematic plan view of a first side 10 of a module similar to that shown in FIG. 8. FIG. 19B shows a schematic plan view of a second side 12 of a module similar to that shown in FIG. 8. Unlike the embodiment illustrated in FIG. 8, the embodiment illustrated in FIGS. 19A and 19B includes a battery holder 110. The battery holder 110 can be configured to receive a battery to keep the battery in place. The battery may slide into an opening of the battery holder 110. As with other embodiments, the module 2 may include electronic components on the substrate 4. For example, the module 2 includes an antenna assembly 18, a memory device 62 and an indicator 70, among other elements. Also, as with other embodiments, the substrate 4 may include one or more contacts 84 and traces 108 among other features.

Although disclosed in the context of certain embodiments and examples, it will be understood by those skilled in the art that the present invention extends beyond the specifically disclosed embodiments to other alternative embodiments and/or uses and obvious modifications and equivalents thereof. In addition, while several variations have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the present disclosure. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the aspects that follow.

What is claimed is:

1. A sensor module for a wearable vital sign monitoring device, the sensor module comprising:
a substrate having a first side and a second side opposite the first side;
a sensor die mounted to the first side of the substrate, the sensor die configured to monitor a vital sign of a user;
an electronic component coupled to or integrated with the second side of the substrate; and
a waterproof coating comprising a first waterproof coating and a second waterproof coating separate from the first waterproof coating, the first waterproof coating conformally covering the sensor die and at least a portion of the first side of the substrate, and the second waterproof coating conformally covering at least a portion of the second side of the substrate,
wherein the first waterproof coating and the second waterproof coating are attached to one another around a periphery of the substrate.

2. The sensor module of claim 1, wherein the electronic component comprises an electrode disposed on the second side of the substrate, the electrode positioned within an opening in the second waterproof coating.

3. The sensor module of claim 2, wherein the sensor die is configured to process signals transduced by the electrode.

4. The sensor module of claim 1, wherein the sensor die comprises an optical sensor.

5. The sensor module of claim 4, wherein the waterproof coating includes a window over a portion of the optical sensor.

6. The sensor module of claim 1, further comprising a battery mounted to the first side of the substrate, the first waterproof coating conformally covering the battery.

7. The sensor module of claim 6, further comprising a battery charging coil electrically connected to the battery.

8. The sensor module of claim 1, further comprising a first cover over the first waterproof coating and a second cover over the second waterproof coating, wherein the first and second covers are joined about the periphery of the substrate such that the substrate is embedded between the first and second covers.

9. The sensor module of claim 8, wherein the second cover comprises a conductive cloth.

10. The sensor module of claim 9, wherein the electronic component comprises an electrode, wherein the electrode is disposed between the conductive cloth and the substrate.

11. The sensor module of claim 1, wherein the substrate and the waterproof coating are flexible.

12. The sensor module of claim 11, wherein the substrate has a flexible radius of 3 cm to 7 cm.

13. A sensor module for a wearable vital sign monitoring device, the sensor module comprising:
a flexible substrate having a first side and a second side opposite the first side;
a plurality of electronic components mounted to the first side of the substrate;
a contact on the second side of the substrate;

a pad comprising an electrode pad or a temperature sensor pad, the pad disposed on the second side of the substrate, the contact configured to electrically connect to the pad;

a flexible waterproof coating comprising a conformal coating, the waterproof coating covering at least a portion of the first side of the substrate, and at least a portion of the second side of the substrate; and a layer conformally covering the pad such that the pad is disposed between the layer and the flexible substrate, the layer comprising an electrically conductive cloth.

14. The sensor module of claim 13, wherein the plurality of electronic components comprise a sensor die configured to process signals transduced by the pad.

15. The sensor module of claim 13, wherein the plurality of electronic components comprise a photodetector and a light emitting diode (LED).

16. The sensor module of claim 15, wherein the waterproof coating includes a window over a portion of the photodetector.

17. A waterproof sensor module, the sensor module comprising:

a substrate having a first side and a second side opposite the first side;

a sensor assembly coupled to or integrated with the substrate;

a conformal coating conformally covering at least a portion of the first side of the substrate, and at least a portion of the second side of the substrate;

a conformal layer conformally covering at least a portion of the conformal coating; and a window through portions of the conformal coating and the conformal layer such that at least a portion of the sensor assembly is free from the conformal coating and the conformal layer.

18. The waterproof sensor module of claim 17, wherein the sensor assembly comprises a processor die and an electrode, wherein the processor die is configured to process signals transduced by the electrode.

19. The waterproof sensor module of claim 17, wherein the sensor assembly comprises a photodetector and a light emitting diode (LED).

20. The waterproof sensor module of claim 17, wherein the conformal coating comprises a conductive cloth.

* * * * *